(12) United States Patent
Vize et al.

(10) Patent No.: US 6,479,285 B1
(45) Date of Patent: Nov. 12, 2002

(54) P53 AS A REGULATOR OF CELL DIFFERENTIATION

(75) Inventors: Peter D. Vize, Austin; John B. Wallingford, Houston, both of TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/108,843

(22) Filed: Jul. 1, 1998

Related U.S. Application Data

(60) Provisional application No. 60/051,549, filed on Jul. 2, 1997.

(51) Int. Cl.$^7$ .................... C12N 5/00; C12N 15/00; C12N 15/63; C07H 21/04
(52) U.S. Cl. ................ 435/377; 435/320.1; 435/325; 435/455; 435/459; 435/461; 435/375; 536/23.1; 536/23.5; 800/21; 800/23; 800/25
(58) Field of Search ................ 435/6, 455, 459, 435/461, 320.1, 325, 375, 377; 424/9.1, 9.2, 93.1, 93.2; 800/21, 23, 25; 536/23.1, 23.5

(56) References Cited

U.S. PATENT DOCUMENTS 5,843,780 A * 12/1998 Thomson .................. 435/363

FOREIGN PATENT DOCUMENTS

| EP | 0518650 | 12/1992 |
|---|---|---|
| WO | WO 91/13150 | 9/1991 |
| WO | WO 92/11874 | 7/1992 |
| WO | WO 93/20238 | 10/1993 |
| WO | WO 95/14777 | 6/1995 |
| WO | WO 97/11367 | 3/1997 |

OTHER PUBLICATIONS

Verma et al., Gene therapy–promises, problems and prospects, 1997, Nature, vol. 389, pp. 239–242.*
Anderson et al., Human gene therapy, 1998, Nature, vol. 392, pp. 25–30.*
Rosenberg et al., Gene therapist, heal thyself, 2000, Science, vol. 287, pp. 1751.*
Keller et al., Human embryonic stem cells: the fiture is now, 1999, Nature Medicine, vol. 5, pp. 151–152.*
Svendsen et al., New prospects for human stem–cell therapy in the nervous system, 1999, Trends Neurosci., vol. 22, pp. 357–364.*
Zanjani et al., Prospects for in utero human gene therapy, 1999, Science, vol. 285, pp. 2084–2088.*
Armstrong et al., "High–frequency developmental abnormalities in p53–deficient mice," *Curr. Biol.*, 5:931–936, 1995.
Carroll and Vize, "Wilms tumor suppressor gene is involved in the development of disparate kidney forms: evidence from expression in the *Xenopus pronephros*," *Dev. Dynamics*, 206:131–138, 1996.

Cho et al., "Crystal structure of a p53 tumor suppressor–DNA complex: understanding tumorigenic mutations," *Science*, 265:346–355, 1994.
Cox,et al., "Xenopus p53 is biochemically similar to the human tumour suppressor protein p53 and is induced upon DNA damage in somatic cells," *Oncogene*, 9:2951–2959, 1994.
Dittmer et al., "Gain–of–function mutations in p53," *Nature Genetics*, 4:42–46, 1993.
Donehower and Bradley, "The tumor suppressor p53," *Biochim. Biophys. Acta*, 1155:181–205, 1993.
Donehower et al., "Mice deficient for p53 are developmentally normal but susceptible to spontaneous tumours," *Nature*, 356:215–221, 1992.
Dong et al., "AP–1/jun is required for early Xenopus development and mediates mesoderm induction by fibroblast growth factor but not by activin," *J. Biol. Chem.*, 271:9942–9946, 1996.
Eliyahu et al., "Overproduction of p53 antigen makes established cells highly tumorigenic," *Nature*, 316:158–60, 1985.
Ferkol et al., "Regulation of the phosphoenolpyruvate carboxykinase/human factor IX gene introduced into the livers of adult rats by receptor–mediated gene transfer", *FASEB J.*, 7:1081–1091, 1993.
Finlay et al., "The p53 proto–oncogene can act as a suppressor of transformation," *Cell*, 57:1083–1093, 1989.
Gottlieb and Oren, "p53 in growth control and neoplasia," *Biochem. Biophys. Acta*, 1287:77–102, 1996.
Haffner and Oren, "Biochemical properties and biological effects of p53," *Curr. Op. Genet. Dev.*, 1995, 5:84–90.
Hall and Lane, "Tumor suppressors: a developing role for p53?," *Curr. Biol.*, 7:R144–R147, 1997.
Harvey et al., "A mutant p53 transgene accelerates tumour development in heterozygous but not nullizygous p53–deficient mice," *Nature Genetics*, 9:305–311, 1995.
Haupt et al., "Mdm2 promotes the rapid degradation of p53," *Nature*, 387:296–299, 1997.

(List continued on next page.)

*Primary Examiner*—Scott D. Priebe
*Assistant Examiner*—Sumesh Kaushal
(74) *Attorney, Agent, or Firm*—Fulbright & Jaworski

(57) ABSTRACT

The present invention involves the role of p53 in the differentiation of embryonic tissues. More particularly, the present invention provides methods of the blocking of p53 function in embryonic tissues, and the use of these tissues as screening tools for substances that are capable of overcoming the p53-related block in differentation, both in vitro and in vivo. The similarities between undifferentiated embryonic cells and tumor cells is evident, and thus these assays serve as a model for possible cancer therapeutics. In addition, methods for identifying additional cellular components that interact p53 or p53-related pathways are provided.

13 Claims, 7 Drawing Sheets

OTHER PUBLICATIONS

Hoever et al., "Overexpression of wild–type p53 interferes with normal development in *Xenopus laevis* embryos," *Oncogene*, 9:109–120, 1994.

Jenkins et al., "Cellular immortalization by a cDNA clone encoding the transformation–associated phosphoprotein p53," *Nature*, 312:651–654, 1984.

Jones et al., "Rescue of embryonic lethality in Mdm2–deficient mice by absence of p53," *Nature*, 378:206–208, 1995.

Komarova et al., "Transgenic mice with p53–responsive lacZ: p53 activity varies dramatically during normal development and determines readiation and drug sensitivty in vivo," *EMBO J.*, 16:1391–1400, 1997.

Kubbutat et al., "Regulation of p53 stability in Mdm2", *Nature*, 387:299–303, 1997.

Kussie et al., "Structure of the MDM2 oncoprotein bound to the p53 tumor suppressor transactivation domain," *Science*, 274:948–953, 1996.

Mercer et al., "Negative growth regulation in a glioblastoma tumor cell line that conditionally expresses human wild–type p53," *Proc. Natl. Acad. Sci. USA*, 87:6166–6170, 1990.

Momand et al., "The mdm–2 oncogene product forms a complex with the p53 protein and inhibits p53–mediated transactivation," *Cell*, 69:1237–1245, 1992.

Montenarh, "Biochemical properties of the growth suppressor/oncoprotein p53," *Oncogene*, 7(9):1673–1680, 1992.

Montes de Oca Luna et al., "Rescue of early embryonic lethality in mdm2–deficient mice by deletion of p53," *Nature*, 378:203–206, 1995.

Newport and Kirschner, "A major developmental transition in early Xenopus embryos: II. Control of the onset of transcription," *Cell*, 30:687–696, 1982b.

Nigro et al., "Mutations in the p53 gene occur in diverse human tumor types," *Nature*, 342:705–708, 1989.

Parada et al., "Cooperation between gene ecoding p53 tumour antigen and ras in cellular transformation," *Nature*, 312:649–651, 1984.

Rotter et al., "Does wild–type p53 play a role in normal cell differentiation?," *Sem. Cancer Biol.*, 5:229–236, 1994.

Sah et al., "A subset of p53 deficient mice exhibit exencephally," *Nature Genetics*, 10:175–180, 1995.

Scheffner et al., "The E6 oncoprotein encoded by human papillomavirus types 16 and 18 promotes the degradation of p53", *Cell*, 63:1129–1136, 1990.

Scheffner et al., "the HPV–16 E6 and E6–AP complex functions as a ubiquitin–protein ligase in the ubiquitination of p53", *Cell*, 75:495–505, 1993.

Schmid et al., "Expression of p53 during mouse embryogenesis," *Development*, 113:857–865, 1991.

Shaulusky et al., "Involvement of wild–type p53 in pre–B–cell differentiation in vitro," *Proc. Natl. Acad. Sci. USA*, 88:8982–8986, 1991.

Sun et al., "Dosage dependent dominance over wild–type p53 of a mutant p53 isolated from nasopharyngeal carcinoma," *FASEB J.*, 7:944–950, 1994.

Suzuki et al., "The p53 gene is very frequently mutated in small–cell lung cancer with a distinct nucleotide substitution pattern," *Cancer Res.*, 52:734–736, 1992.

Tchang et al., "Stabilization and expression of high levels of p53 during early development in *Xenopus laevis*," *Dev. Biol.*, 159:163–172, 1993.

Wang et al., "*Xenopus laevis* p53 protein: sequence–specific DNA binding, transcriptional egulation and oligomerization are evolutionarily conserved," *Oncogene*, 19:779–784, 1995.

Wallingford et al., "Precocious Expression of the Wilms' Tumor Gene xWT1 Inhibits Embryonic Kidney Development in *Xenopus laevis*," *Dev. Biol.*, 202:103–112, 1998.

Wallingfrod et al., "p53 is essential for normal development in Xenopus," *Current Biology*, 7:747–757, 1997.

Whitman and Melton, "Involvement of p21ras in Xenopus mesoderm induction," 357:252–254, 1992.

Yang et al., "p63, a p53 Homolog at 3q27–29, Encoded Multiple Products with Transactivating, Death–Inducing, and Dominant–Negative Activities," *Molecular Cell*, 2:305–316, 1998.

Yew and Berk, "Inhibition of p53 transactivation required for transformation by adenovirus early 1B protein", *Nature*, 357, 82–85, 1992.

Sabapathy et al., "Regulation of ES differentiation by functional and conformational modulation of p53," *EMBO J.*, 16(20):6217–6219, 1997.

pg,10

Brodsky et al., "Drosophila p53 binds a damage response element at the reaper Locus," *Cell*, 101:103–113, 2000.

Derry et al., "Caenorhabditis elegans p53: role in apoptosis, meiosis, and stress resistance," *Science*, 294:591–595, 2001.

Ollmann et al., "Drosophila p53 is a structural and functional homolog of the tumor suppressor p53," *Cell*, 101:91–101, 2000.

Schumacher et al., "The C. elegans homolog of the p53 tumor suppressor is required for DNA damage–induced apoptosis," *Current Biology*, 11:1722–1727, 2001.

* cited by examiner

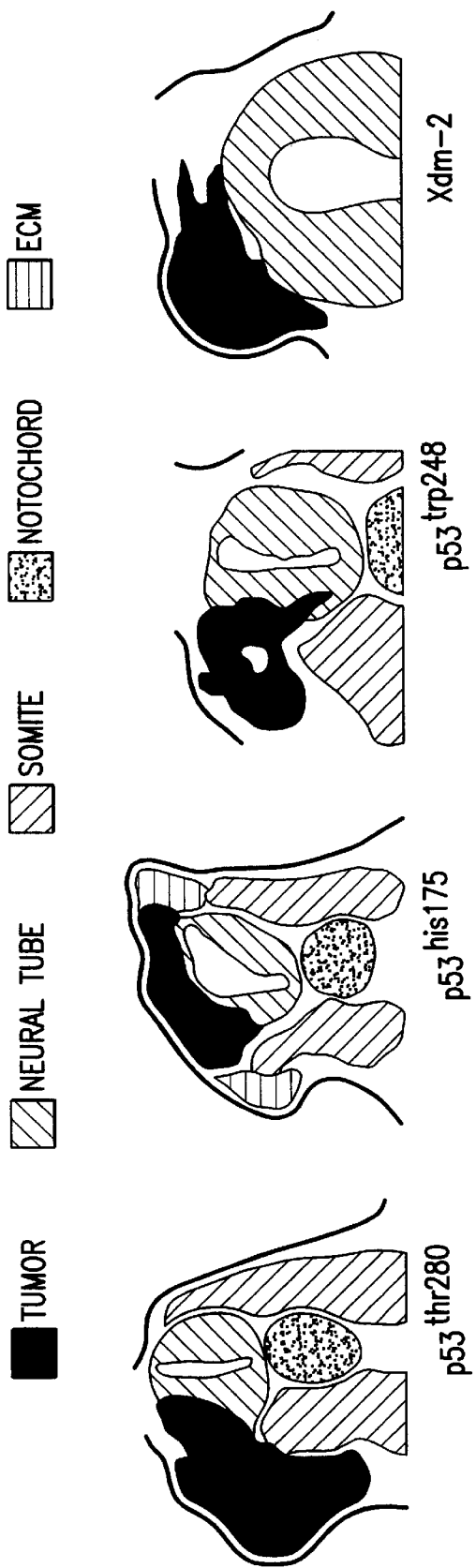

SEQUENCE LISTING

<160> NUMBER OF SEQ ID NOS: 6

-continued

```
<210> SEQ ID NO 1
<211> LENGTH: 20
<212> TYPE: DNA
<213> ORGANISM: Homo sapiens

<400> SEQUENCE: 1
cagattggtg ctggatatgc                                              20

<210> SEQ ID NO 2
<211> LENGTH: 20
<212> TYPE: DNA
<213> ORGANISM: Homo sapiens

<400> SEQUENCE: 2
actgccttga tgactcctag                                              20

<210> SEQ ID NO 3
<211> LENGTH: 18
<212> TYPE: DNA
<213> ORGANISM: Homo sapiens

<400> SEQUENCE: 3
acaactggaa gcactgga                                                18

<210> SEQ ID NO 4
<211> LENGTH: 18
<212> TYPE: DNA
<213> ORGANISM: Homo sapiens

<400> SEQUENCE: 4
tcttattcca gaggaacc                                                18

<210> SEQ ID NO 5
<211> LENGTH: 18
<212> TYPE: DNA
<213> ORGANISM: Homo sapiens

<400> SEQUENCE: 5
ggatcgttat cacctctg                                                18

<210> SEQ ID NO 6
<211> LENGTH: 18
<212> TYPE: DNA
<213> ORGANISM: Homo sapiens

<400> SEQUENCE: 6
gtgtagtctg tagcagca                                                18
```

P53 AS A REGULATOR OF CELL DIFFERENTIATION

This application is a non-provisional application of provisional Serial No. 60/051,549, filed Jul. 2, 1997.

The government may own certain rights in this invention pursuant to a grant number IBN-9630621 from the National Science Foundation.

BACKGROUND OF THE INVENTION

A. Field of the Invention

The present invention relates generally to the fields of oncology, embryology, molecular biology and genetics. More specifically, the invention relates to the tumor biology of p53 mutants, molecules that interact with p53, and agents that are able to block p53-related defects in cellular differentiation.

B. Description of Related Art

Many mutant p53 alleles are oncogenic, and p53 was in fact first thought to be an oncogene as the first clones isolated corresponded to mutant forms expressed in immortalized cell lines. Expression of mutant p53 immortalizes primary fibroblasts, and in combination with mutant ras, transforms such cells (Jenkins et al., 1984; Parada et al., 1984; Eliyahu et al., 1985). Normal p53, however, functions as a tumor suppressor and its overexpression can inhibit the growth of various tumor cell lines and can block the transforming activity of a variety of oncogenes (Finlay et al., 1989; Donehower and Bradley, 1993).

p53 possesses several different biochemical activities, including transcriptional activation and repression, single-stranded DNA binding, and interaction with several heterologous proteins (Donehower and Bradley, 1993; Gottlieb and Oren, 1996; Haffner and Oren, 1995). These activities regulate a diverse array of biological processes, for example cell cycle transitions, apoptosis, and response to DNA damage (Donehower and Bradley, 1993; Gottlieb and Oren, 1996; Haffner and Oren, 1995). Elimination of p53 activity is thought to contribute to the initiation or progression of tumorigenesis by loss of cell cycle control, genomic instability, and the acquisition of novel properties, such as resistance to hypoxia (Donehower and Bradley, 1993; Gottlieb and Oren, 1996; Haffner and Oren, 1995; Graeber et al., 1996). Given this involvement in numerous fundamental processes, it is quite surprising that p53-null mice develop to term in the majority of cases (Donehower et al., 1992; Armstrong et al., 1995; Sah et al., 1995). However, p53 is expressed during early murine development in a pattern consistent with a role in differentiation (Schmid et al., 1991; Komarova et al., 1997), and the precise regulation of expression appears to be essential for normal development (Montes de Oca Luna et al., 1995; Jones et al., 1995).

Thus, although it is clear that p53 plays a key role in tumor development, and may be involved in differentiation as well, the particular mechanisms by which this molecule functions remain undefined. Moreover, it is unclear whether the role play by p53 in these two activities is related.

SUMMARY OF THE INVENTION

The present invention involves the role of p53 in the differentiation of embryonic tissues. More particularly, the present invention provides methods of the blocking of p53 function in embryonic tissues, and the use of these tissues as screening tools for substances that are capable of overcoming the p53-related block in differentiation, both in vitro and in vivo. These assays serve as a model for possible cancer therapeutics. In addition, methods for identifying additional cellular components that interact p53 or p53-related pathways are provided.

There is provided in the present invention a method of screening for agents that inhibit a p53-related block of embryonic cell differentiation comprising the steps of providing an undifferentiated embryonic cell; blocking the function of p53 in the cell such that the cell fails to differentiate; contacting the cell with a candidate agent; and comparing the differentiation of the contacted cell after the contacting with the differentiation of the cell in the absence of the candidate agent whereby an increase in differentiation indicates that the candidate agent is an inhibitor of the p53-related block of differentiation.

In particular embodiments, the method further comprises the step of comparing the differentiation of the cell after the contacting with the differentiation of the undifferentiated embryonic cell. In more particular embodiments, the cell may be an amphibian cell. In still more particular embodiments, amphibian cell is a *Xenopus laevis* cell. In other specific embodiments, the cell is an insect cell. In more particular embodiments, the insect cell is a *Drosophila melanogaster* cell. In further embodiments, it is contemplated that the cell may be a mammalian cell. In specific embodiments the cell may be a mouse cell, in alternate embodiments the mammalian cell is a human cell.

In particular aspects, the blocking is achieved by introducing into the cell a nucleic acid encoding a dominant negative mutant of p53. More specifically, the introducing may be achieved via electroporation, microinjection, particle bombardment, liposome transfer or viral infection. In certain aspects, the nucleic acid is a DNA; in other aspects, the nucleic acid is an RNA.

In certain specific embodiments, the blocking is achieved by introducing into the cell a nucleic acid encoding double minute-2 or a ortholog thereof. In other embodiments, the blocking is achieved by introducing into the cell an antisense nucleic acid for p53. In specific aspects, the candidate agent is a nucleic acid. In other embodiments, the candidate agent is polypeptide. In particular embodiments, the candidate agent is produced by a neighboring cell. In other embodiments, the neighboring cell is a second undifferentiated embryonic cell into which the candidate agent has been introduced.

In particular aspects, the differentiation is determined by culture of the undifferentiated embryonic cell in vitro under conditions where the cell differentiates.

More particularly the differentiation is determined by development of an embryo in vitro or in vivo.

Also provided is a method for identifying genes involved in p53-mediated embryonic cell differentiation comprising the steps of providing a plurality of undifferentiated *Drosophila melanogaster* embryonic cells; contacting the cells with a gene encoding a dominant negative mutant of p53 operably linked to a developmentally regulated promoter responsible for a given trait; mutagenizing the contacted cells; assessing development of the trait in the resulting flies; and determining the identity of a mutated cellular product in flies exhibiting trait development.

In certain embodiments, the mutagenizing may comprise radiation of the cells. In other embodiments, the mutagenizing may comprise contacting the cells with a DNA damaging agent. In still further embodiments, the mutagenizing comprises introducing mRNA into the cells.

In particular aspects of the present invention, the contacting comprises microinjection of a P-element comprising the mutant p53 gene and the promoter. In particular aspects, the promoter is the eyeless promoter and the trait is eye development.

In other aspects of the present invention, there is provided a method for identifying genes involved in p53-mediated embryonic cell differentiation comprising the steps of providing a plurality of pluripotent embryonic stem cells transformed with a gene encoding a dominant negative mutant of p53 operably linked to an inducible promoter; contacting the cells with nucleic acid encoding a polypeptide and a factor that induces the inducible promoter; culturing the contacted cells under conditions permitting differentiation; and assessing the differentiation of the cells, wherein differentiation in a cell identifies a polypeptide involved in p53-mediated cell differentiation.

In preferred aspects, the method further comprises contacting the cells with a plurality of nucleic acids encoding polypeptides. In certain embodiments, the plurality of nucleic acids is an expression vector library.

In particular embodiments, the inducible promoter is the ecdysone response promoter and the factor is ecdysone. In alternate embodiments, the inducible promoter is the metallothionein promoter and the factor is a heavy metal. In yet another embodiment, the inducible promoter is the tetracycline promoter and the factor is tetracycline. In still another alternative embodiment, the inducible promoter is a heat shock promoter and the factor is heat.

In particular aspects, the conditions include culture without LIF. In preferred embodiments, the differentiation comprises formation of hematopoietic cells, macrophages and cardiac cells. In other embodiments, the conditions further include culture on bacterial grade plastic and the differentiation comprises formation of erythroid cells. In other embodiments the conditions further include culture with retinoic acid and the differentiation comprises formation of neural cells. In still another embodiments, the conditions further include culture with erythropoietin and the differentiation comprises formation of hematopoietic cells. In a further alternative embodiments, the conditions further include culture with interleukin 3 and the differentiation comprises formation of macrophages, neutrophils and mast cells. In yet another alternative, the conditions further include culture with interleukin 3, interleukin 1, and macrophage colony stimulating factor or granulocyte-macrophage colony stimulating factor and the differentiation comprises macrophages. In other embodiments, the conditions further include culture with bone morphogenetic protein 4 and the differentiation comprises hematopoietic cells.

In particular aspects, the the embryonic stem cells are mammalian cells. The mammalian cells may be mouse cells. In those embodiments, where the cells are mouse cells, the culturing may comprise injected the contacted cells into a mouse blastocyst and implanting the blastocyst in a foster mother. Alternatively, the mammalian cells are human cells. In other preferred embodiments, the embryonic stem cells are amphibian cells. In particular embodiments, the amphibian cells are *Xenopus laevis* cells. In an alternate preferred embodiments the embryonic stem cells are insect cells. More particularly the insect cells may be *Drosophila melanogaster* cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 1A. Experimental protocol. Xenopus embryos were fertilized in vitro. At the 32-cell stage, a single blastomere was either co-injected with β-galactosidase and mutant p53 mRNAs, or injected with β-galactosidase alone. Embryos were injected into one side only, allowing the uninjected side to act as an internal control for normal development. Injected embryos were reared to the swimming tadpole stage, fixed, and stained to detect the presence of β-galactosidase activity. Cells expressing $p53^{Thr280}$ and β-galactosidase (light blue) did not contribute to normal embryonic structures and clumped together into large cell masses, or tumors (arrows). FIG. 1B. Transverse section through an embryo injected with β-galactosidase and $p53^{Thr280}$ mRNAs. The tumor is continuous with the spinal cord and is partially covered by pigmented melanocytes (red arrows), as is the spinal cord. Note that the somite ventral to the tumor is reduced in size compared to the somite on the uninjected (control) side. Specimen stained with hematoxylin and eosin. FIG. 1C. Transverse section through the same specimen as in B, stained with Sytox green to visualize nuclei. The tumor is nucleated and contains cells of approximately normal size. FIG. 1D. Transverse section through an embryo injected with $p53^{Thr280}$ and β-galactosidase mRNAs and stained with the neural-specific antibody 2G9 (dark purple histochemical substrate). The spinal cord is strongly stained, but the tumor cells (black arrows, light blue/green stain), including those intimately associated with the spinal cord, do not express the antigen. A melanocyte associated with the tumor is indicated with a red arrow.

FIG. 2A—Embryo injected with 125 pg of $p53^{Thr280}$ mRNA plus β-galactosidase mRNA and stained for β-galactosidase activity; cells expressing β-galactosidase (blue) clump together into distinct cell masses or tumors (arrow). FIG. 2B—Embryo injected with 125 pg $p53^{Thr280}$ plus 500 pg of human wild-type p53 and β-galactosidase as a lineage tracer; cells expressing β-galactosidase are distributed normally across the embryo and incorporated into normal tissues.

FIG. 3A, FIG. 3B, FIG. 3C, FIG. 3D, FIG. 3E, FIG. 3F, FIG. 3G, and FIG. 3H. Morphology of developmental tumors (transverse sections). The left side of embryo was injected in all cases. Schematic representation of each panel is shown below in 3E–H. FIG. 3A—$p53^{Thr280}$-induced tumor. The tumor bulges out from the lateral surface of the spinal cord. The somite on the injected side is restricted ventrally (compare to uninjected control side). FIG. 3B—$p53^{His175}$-induced tumor. The tumor is continuous with the dorsal spinal cord and the overlying epidermis, and occupies much of an extracellular-matrix-filled space lateral to the spinal cord where the somite is normally present. FIG. 3C—$p53^{TrP248}$-induced tumor. The tumor is integrated into the dorsal neural tube and extends ventrolaterally where somite is normally present. FIG. 3D—Xdm-2 induced tumor. The tumor is integrated into the epidermis dorsal to the hindbrain. Tumors in all cases contain a high density of yolk platelets and appear to be undifferentiated. Scale bar= 100 microns. Scale is similar in A–C. ecm=extracellular matrix.

DETAILED DESCRIPTION OF THE PREFERRED EMBODIMENT

Figure 1A:
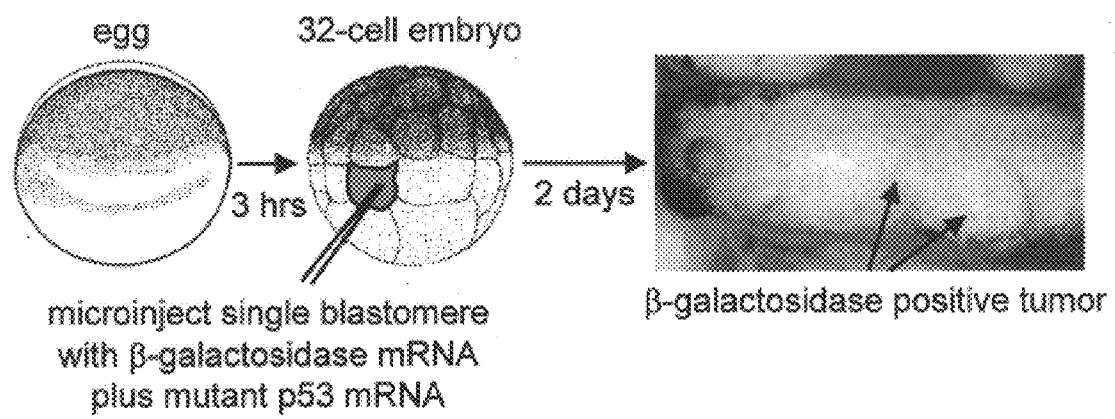
FIG. 1A, FIG. 1B, FIG. 1C and FIG. 1D. Expression of dominant-negative p53 inhibits differentiation and results in the formation of developmental tumors.
Figure 1B:
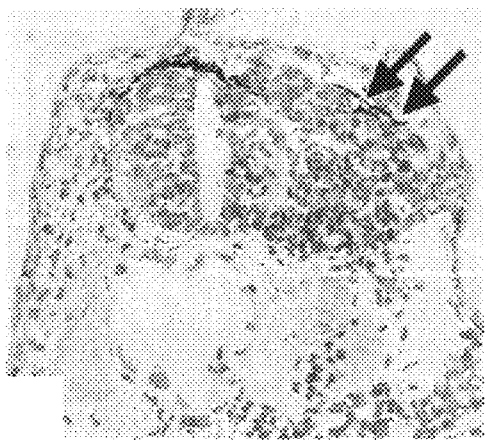
Figure 1C:
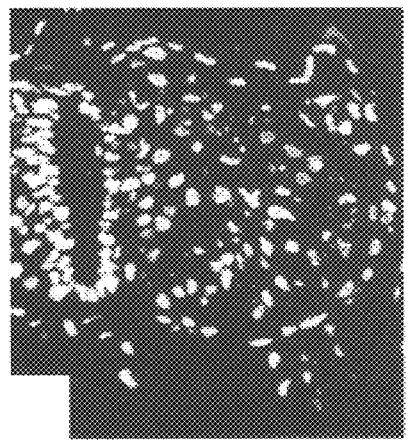
Figure 1D:
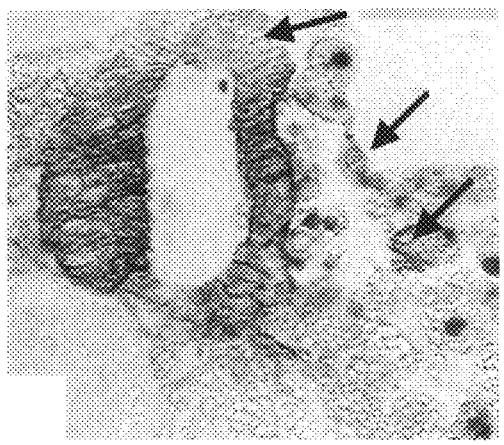

Cancer accounts the death of over half a million people each year in the United States alone. The causes for cancer are multifactorial, however, it is known that aberrations in controlled cell death result in uncontrolled cell proliferation and hence contribute to many cancer. The p53 gene is well recognized as possessing tumor suppressor capabilities and mutations in wild-type p53 are correlated to a variety of cancers. However, the interaction of p53 with other cellular factors is not well characterized, and in fact, many of these factors remain undefined. It is not surprising that, in light of the lack of significant information on p53 function, there is an incomplete understanding of the pathways through which p53 regulates tumor development.

A. The Present Invention

The present inventors have examined the role of p53 in differentiation of cells as a way of better understanding the growth regulatory properties of this molecule. It now has been demonstrated that blocking p53 function in embryonic cells halts differentiation. By using different kinds of p53 mutations and by differing blocks to p53 function, one can assess the different functional aspects of p53 as it relates to differentiation. Furthermore, one can use differentiation as a measure of different agents to overcome this p53-mediated block in differentiation.

Certain biological systems are particularly well-adapted to exploit this approach. For example, the developmental biology of Xenopus and Drosophila are extremely well characterized, easily reproduced, and suitable for large scale screening methods. Murine systems also provide a fruitful, if somewhat more complex, system in which to explore the functions of p53. In addition, it is anticipated that human embryonic cells may be utilized in vitro for various of the experiments described herein.

In general terms, the present invention decribes blocking differentiation in embryonic cells by inhibiting, mutating, blocking, or otherwise abrogating p53 activity. The differentiation ability of the cells may be rescued by introducing a gene, gene product or phamaceutical compound which can bypass the mutant p53 mediated block and identifying those cells which have undergone differentiation in the presence of mutant p53.

In particular, it is anticipated that one can screen large numbers of potential pharmaceuticals, small molecule libraries and expression libraries for active compounds. The compounds will be screened for their ability to permit differentiation of cells which otherwise remain undifferentiated. The dysplastic nature of these cells is remarkably similar to that of tumor cells arising from p53 defects, and thus the overcoming of this block appears, in certain aspects, analogous to treatment of tumors, although most conventional treatments are designed to kill tumors, not correct defects. Thus, it is believed that the present invention provides a unique approach to the identification of factors, exogenous and endogenous, that can serve as therapeutics for cancers and other developmentally-related diseases.

B. p53 Polypeptides and Nucleic Acids Coding Therefor p53 currently is recognized as a tumor suppressor gene (Montenarh, 1992). High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al., 1991) and in a wide spectrum of other tumors.

The p53 gene encodes a 393-amino-acid phosphoprotein that can form complexes with viral proteins such as. large-T antigen and E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or activate genes that suppress this growth. Thus, absence or inactivation of wild-type p53 may contribute to transformation. However, some studies indicate that the presence of mutant p53 may be necessary for full expression of the transforming potential of the gene.

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects. It is thus proposed that the treatment of p53-associated cancers with wild type p53 will reduce the number of malignant cells or their growth rate. Clinical. data using retroviral p53 to treat cancer also have been presented (Roth et al., 1996)

i) p53 in Differentiation

Observations from both transgenic mice and tissue culture experiments have raised the possibility that p53 may be required for normal differentiation in some cell types. Foremost among these observations is the high incidence of neural tube and craniofacial abnormalities observed in p53-null mice (Armstrong et al., 1995; Sah et al., 1995). Other observations consistent with a developmental role include the under-representation of transgenic mice in the offspring of transgenics containing mutant p53 alleles (Harvey et al., 1995) and a possible involvement of p53 in B-cell differentiation (Hall and Lane, 1997; Rotter et al., 1994). These results suggest that either p53 plays a role in some aspect of differentiation, or that the lack of p53 activity results in the accumulation of genetic lesions which in turn inhibit normal development.

The Xenopus embryo provides an excellent model for the rapid development of embryonic cells. Xenopus p53 is biochemically and biologically similar to human p53 (Cox et al., 1994), and Xenopus embryos contain a ubiquitous maternal stockpile of p53 mRNA, and protein (Hoever et al., 1994; Tchang et al., 1993). Elimination of protein function in Xenopus has been most effectively achieved by overexpression of dominant-negative mutants (Hemmatti-Brivanlou and Melton, 1992; Levine et al., 1994; Molenaar et al., 1996; Dong et al, 1996), and many mutant forms of p53 have been shown to act in a dominant-negative manner (Baker et al., 1989; Nigro et al., 1989).

ii) Methods of InhibitingpS3 Function

According to the present invention, one will seek to block the expression and/or function of p53 as it relates to differentiation of embryonic cells. In so doing, cells engineered or treated in this manner will have a p53-mediated block in differentiation. This accomplished, it then remains to determine what factors are capable of overriding this effect.

Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, these "dominant negative" alleles appear to be tolerated in the organism and passed on in the germ line. Various mutant alleles appear to range from minimally dysfunctional to strongly penetrant, dominant negative alleles (Weinberg, 1991).

In one embodiment, blocking of p53 function is achieved by providing to a cell containing a wild-type p53 gene a dominant negative mutant of p53. Unlike some p53 mutants, which merely are inactivated (i.e., lacking the normal tumor suppressor function) and can be rescued by provision of a wild-type gene, dominant negative mutants will "override" the actions of a wild-type gene. Thus, no "knock-out" or other anti-p53 modifications are required, only the provision of a dominant negative mutant.

Typically, this is achieved by transforming a cell (discussed further, below) with a gene encoding a dominant negative mutant of p53. Below (Table 1), there is listed a series of p53 mutants that function as dominant negative mutants.

TABLE 1

Dominant Negative p53 Mutants

| Mutation | Location | Classification |
| --- | --- | --- |
| Arg→His | 175 | dominant negative |
| Arg→Trp | 248 | dominant negative |
| Arg→Thr | 280 | dominant negative |

Another method of blocking p53 function, in a manner similar to that discussed above, is the provision of a p53 binding protein that will inactivate wild-type p53 that is present in the embryonic cell. Such a binding protein is the so-called "double minute-2," a oncoprotein that binds to and inhibits the transcriptional activation domain of p53. Orthologs have been identified in the mouse (mdm-2), Xenopus (Xdm-2) and human (Oliner et al., 1992). MDM-2 also can inhibit p53 activity by targeting the p53 protein for ubiquitin-mediated degradation (Kubbutat et al, 1997; Haupt et al., 1997).

Inhibition of p53 activity also may be achieved by expression of p53-binding proteins encoded by viral oncogenes. One such protein is the E6 protein of human papillomvirus types 16 or 18. This protein binds to p53, and in combination with the a cellular protein, the 100 kd E6 asssociated protein (E6-AP), targets p53 protein for ubiquitin-mediated degradation (Scheffner et al., 1990; 1993). One could envision expressing either E6 alone or E6 in addition to E6-AP in order to inhibit p53 activity. Likewise, the adenovirus 55K early 1B (E1B 55K) protein binds to p53 and inhibits its transcriptional activation activity and its tumor suppressor functions (Sarnow et al., 1982; Yew and Berk, 1992). Expression of EIB therefore also may be used to inhibit p53 activity in the present invention.

In various other embodiments, one may utilize antisense methodologies to inhibit the expression of p53. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to formn combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

Yet another manner of disrupting normal p53 function in a cell is to provide that cell with a ribozyme construct that cleaves wild-type p53 transcripts, thereby preventing translation of a complete p53 product. Although proteins traditionally have been used for catalysis of nucleic acids, another class of macromolecules has emerged as useful in this endeavor. Ribozymes are RNA-protein complexes that cleave nucleic acids in a site-specific fashion. Ribozyme s have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., :1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

C. Expression Constructs

According to the present invention, various genes will be expressed, both in vitro and in vivo. Synthetic mRNA encoding a gene product of interest, or a pool of synthetic mRNAs generated from a pool of template DNAs can be synthesized in vitro using purified bacterial or bactiophage RNA polymerases. Such mRNA(s) can be introduced into cells directly by microinjection or by any of the transfection methods used to introduce DNA into a cell. In order to enhance the translation of synthetic mRNA in a cell it is important to synthesize the mRNA incorporating a 5' cap. cDNAs to be translated into mRNA are also often cloned into specific vectors which contain 5' and 3' untranslated sequences from efficiently translated mRNAs to enhance the translational efficiency of the synthesized mRNA. Sequences which enhance the polyadenylation of introduced mRNAs are also sometimes incorporated into vectors used for in vitro mRNA synthesis.

Expression of genes of interest calls for the use of expression vectors which provide for the replication, amplification and expression of constructs contained therein. Replication and amplification usually require an origin of replication. Expression requires appropriate signals in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located-in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

In particular embodiments, the present invention encompasses the use of Drosophila promoters such as eyeless. In this context, the promoters are associated with development of various traits and hence may be classified as "tissue specific" promoters, i.e., is expressed in certain tissues and not others.

Enhancers are genetic elements that increase transcription from a promoter located at a distant position. on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are. often overlapping and contiguous, often seeming to have a very similar modular organization. Any promoter/enhancer combination (as per the Eukaryotic Promoter Data Base EPDB) could also be used to drive expression of the gene.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

ii) Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually, the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Alternatively, the markers may be utilized simply for identification purpose. Enzymes that provide fluorimetric or calorimetric changes include β-galactosidase, green fluorescent protein and luciferase. Further examples of markers are well known to one of skill in the art.

iii) Multigene Constructs and IRES

In certain embodiments of the invention, the use of internal ribosome entry site (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or memrbrane-bound proteins and selectable markers. In this way, expression of several proteins can be simultaneously engineered into a cell with a single construct and a single selectable marker.

iv) Viral Vectors

Another useful variation of the expression vector is the viral vector. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express a polynucleotide (sense or antisense) that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products-of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al, 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest also may be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genorne in the place of certain viral sequences to produce a virus that is replication-defective. In order to produce virions, a packaging cell line containing the gag, pol, and env genes but without the LTR and packaging components is constructed (Mann et al; 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Bajchwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

D. Methods of Transforming Cells

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use. RNA compositions also may be delivered to cells using these methods. RNA, for example, a pool of in vitro synthesized mRNA may be complexed similarly to the DNA complexes described above, for delivery into cells.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet futher embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

The introduction of DNA, mRNA or protein into cells by microinjection can be used to screen for molecules capable of imparting novel characteristics to the injected cell, or to rescue defects in the injected cell. Microinjection is performed by puncturing the cell with an injection needle or pipette containing the DNA, mRNA or protein of interest, and forcing a portion of these contents into the cell by applying positive pressure. In Xenopus embryos the most commonly introduced material is in vitro synthesized mRNA (Vize etal., 1991), but expression plasmids and even antibodies also may be used. The basic experiment is performed by:

1. Performing an in vitro fertilization of Xenopus eggs;
2. removing the jelly coat of the fertilized embryos;

3. culture of embryos in a simple saline solution until the required stage. This is usually somewhere between the 2 cell stage (approx. 80 minutes post-fertilization) and the 64-cell stage;
4. embrydos are placed in a solution of Ficoll then microinjected with the molecule(s) of interest
5. embryos are allowed to recover in Ficoll solution for a number of hours then returned to simple saline buffer
6. embryos are raised to the stage of interest then examined for an effect of the injected molecules by analyzing gene expression in repose to the introduced molecule(s) or by analyzing the morphology of the embryo in response to the introduced molecule(s).

In certain embodiments, the inventors contemplate introducing a molecule that alters the developmental fate of an embryonic cell. The cells at the animal pole (the top, darkly pigmented portion) of Xenopus embryos will normally form the epidermis and neural tissue of the tadpole, and the frog which will develop from the tadpole. The animal pole can be cut off from an early stage embryo and cultured in a simple saline solution in isolation from the remainder of the embryo. Under such circumstances the animal pole will differentiate into a ball of epidermal cells. The cells have not yet received the necessary signals from the bottom half of the embryos which instruct a portion of the animal pole cells to form the nervous system. Such animal pole explants do not form any mesodermal tissue, such as muscle or notochord. The animal pole cells are naive embryonic cells: they are not yet differentiated but have the potential to form many different types of cell.

The ability of a gene or gene product to encode a specific pathway of differentiation can be tested by introducing the gene into the animal pole of an early embryo. If the animal pole of such an embryo is then removed and cultured in isolation the ability of the injected molecule to alter cell fate from epidermal (the default) can be examined. For example, the Brachyury gene plays a key role in the development of mesodermal cells, including muscle. If an mRNA encoding Brachury is injected into the animal pole of early Xenopus embryos, the embryos are grown to blastula stage, and the animal pole is removed and cultured in isolation, the pole cells will differentiate into both epidermal cells (the default) and mesodermal cells including muscle cells. The differentiation of muscle can be detected by assaying for the expression of muscle specific gene expression or by histology to directly visualize the formation of embryonic muscle blocks, or somites (O'Reilly et al., 1995).

Pools of mRNA from embryonic tissue also can be microinjected into the animal pole and induce the formation of cells which would not normally form in isolated animal cells. Examples include ovary mRNA and mRNA from Xenopus cultured cell lines which leads to the formation of mesodermal cells (Woodland and Jones, 1987). Although such complex pools have not been fractionated to yield specific gene products with mesoderm inducing activities (these mesoderm inducing molecules were identified by other means making the screen redundant) such a screen is very feasible.

In other embodiments, the inventors contemplate rescue of an embryonic deficiency by microinjection of mRNA. Defects in embryos can be rescued by supplying the defective embryo with a gene product capable of providing, or compensating for, factors missing in the embryo. A commonly used system in Xenopus is the generation of ventralized embryos by irradiating early embryos with ultraviolet light. The UV light disrupts cytoplasmic rearrangements which under normal circumstances lead to the activation of genes required for the development of dorsal cell types. Such embryos lack dorsal structures such as a head, notochord and muscle.

If UV-irradiated embryos are microinjected with an mRNA encoding a gene capable of directing cells to form dorsal structures, the injected mRNA can rescue the deficiency in such structures and result in normal development. Single cloned gene products with rescuing activity work under such circumstances, for example Xwnt-8, (Sokol et al., 1991, Smith and Harland, 1991), as do complex mixtures of embryonic mRNA enriched for genes expressed in dorsal tissues (Smith and Harland 1992). When complex mixtures of mRNA with UV rescuing activity were identified the fractionation of such mRNA pools eventually led to the identification of novel gene products involved in specifying dorsal development (Smith and Harland, 1991, 1992).

In specific embodiments, the inventors contemplate using a combination of these approaches. The inventors contemplate introduction of a single mRNA (mutant p53) to induce a defect plus a pool of mixed mRNAs which may be able to rescue the defect. By screening hundreds of such complex pools the inventors can identify gene products capable of overriding the requirement for p53 in differentiation. Once such active pools are identified, they can be broken down into subpools which can then be retested. These will once again be broken down until single gene products is identified.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest also may be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al, 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al, (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

E. Assay Formats According to the Present Invention

The present invention involves the monitoring of p53, as a regulator of differentiation, in the screening of compounds for the ability to overcome blocks in p53 function. A variety of different formats are available, utilizing both in vitro and in vivo approaches. These are discussed, generally, below.

i) In vitro

In vitro assays have a distinct advantage over in vivo assays in that the requirements for cell culture are less stringent, and often less expensive, than for in vivo systems. However, they suffer, in some contexts from the fact that whole organism models are, by their very nature, more reflective of the developmental patterns seen in nature. Nonetheless, in vitro models are powerful tools, especially when the screening involves large numbers of compounds.

In a first embodiment, the present invention encompasses the use of pluripotent embryonic cells in various culture assays. These cells may be obtained from the blastocoel of virtually any organism by needle aspiration. Culture of these undifferentiated, totipotent cells is performed in the presence of a factor that will prevent their differentiation. An example of such a factor is LIF or alternatively by culturing on embryonic feeder cells which provides the LIF. In the presence of LIF, embryonic cells remain totipotent and undifferentiated. Removal of LIF from the culture permits differentiation.

Other culture parameters for embryonic stem cells include culture in methylcellulose, fetal calf serum and monothioglycerol, β-mercaptoethanol or other reducing agent.

Depending on other culture conditions, the type of differentiation will vary. For example, ES cells are maintained in LIF or embryonic feeder cells on culture grade plastic. To induce differentiation they are palced on bacterial grade plastic in a medium containing fetal calf serum, and usually a reducing agent for example BME or MTG. The FCS is required for differnetiation to occur. Often, this differentiation is performed in semi-solid media conatining methylcellulose. Variations of these culture conditions which give rise to other cell types are usually variations in tissue culturgrade palstic, methylcellulose semi-solid media, FCS, reducing agents and other chemicals and growth factors. For example, culture with retinoic acid gives rise to neural cells. Culture with erythropoietin causes hematopoietic cells to form. Culture with interleukin 3 causes formation of macrophages, neutrophils and mast cells. Culture with interleukin 3, interleukin 1, and macrophage colony stimulating factor or granulocyte-macrophage colony stimulating factor results in the formation of macrophages. Culture with bone morphogenetic protein 4 gives rise to hematopoietic cells.

Once the culture system is established, one may bring the candidate test substance into contact with the cells. At such a time, the differentiation-inhibiting factor is removed, and the effects of the candidate substance on differentiation are observed. Proper controls include culturing cells in the absence of the factor, but without the candidate substance. Dose range and escalation studies also are contemplated. Depending on the nature of the candidate substance, the contacting may comprise merely coculturing the cells with the substance. Other substances should be delivered to the inside of the cell. This can be accomplished by microinjection or, in the case of nucleic acids, by the methods set forth above.

Sufficient culture time is required following the contacting of the candidate substance with the embryonic cells. Depending on the cell, this time will vary considerably, but the appropriate time may easily be ascertained by removing the differentiation-inhibiting factor from untreated cells and determining the period need for differentiation of these cells into the expected cell type. For murine cells, the typical time is approximately 10 days. Amphibian (Xenophus) cells require, generally, about 2 days, and insect (Drosophila) cells differentiate in about 12 days.

ii) In vivo

An alternative to in vitro assays is an in vivo. While more complex and expensive than in vitro assays, in vivo assays may more accurately reflect the natural state, and thereby provide more accurate information, at least with respect to some properties. A number of different assays are contemplated. The examples discussed below are not intended to be all inclusive of the systems which may be utilized, as virtually any biological system can be adapted for the purposes of the present invention.

1. Xenopus

In one embodiment, the *Xenopus laevis* system is employed. As indicated above, Xenopus p53 is very similar to human p53, and Xenopus embryos contain a ubiquitous maternal stockpile of p53 mRNA and protein. In order to inactivate the endogenous p53, mRNA encoding a dominant negative form of p53 can be microinjected into a single or multiple blastomere(s). Preferred is injection into the 32-cell stage blastomere, into presumptive mesodermal tissue. However, other stages of development also may be employed, for example, 8, 16, 32, 64 or 128 cell stages will work at differing efficiencies. A particular advantage of c lturing Xenopus embryos is that such cultures are markedly less expensive than culturing mammalian cells in vitro.

Alternatively, one can inactive the resident p53 by providing, to the blastomere cell, a double minute-2 oncoprotein. This molecule binds to the transcriptional activation domain of p53 and inactivates its function. Again, mRNA encoding the double minute-2 molecule is injected into the blastomere cell, and expression of the corresponding polypeptide will block p53 function.

Another advantageous embodiment includes the injection into cells of a marker gene. Such a gene permits tracing of the lineage of injected cells in later development. Examples include β-galactosidase, green fluorescent protein and luciferase. When embryos reach tadpole stage, tissues can be fixed and stained, for example, for β-galactosidase activity using an appropriate chromogenic substrate.

Histological analysis of tissues injected with either dominant negative p53 mutants or the double minute-2 oncoprotein show cell masses that resemble tumors and also are reminiscent of undifferentiated embryonic cells. Abnormal nuclear morphologies also were observed. Histologically, these tissues are considered to be blastomas.

According to the present invention, it is contemplated that this model for tumor development can be used to screen for agents that inhibit p53-related tumor development. In various embodiments, candidate inhibitors are contacted with the engineered cells. Depending on the candidate agent, the route of delivery will vary. For example, merely contacting the cell with an organo-pharmnaceutical may be sufficient, whereas the preferred mode of contacting for nucleic acids, both RNA's and DNA's, is to transfer the nucleic acid into the cell. This can be accomplished by any of the techniques mentioned above.

It then remains only to monitor the development of the ensuing tissues, which can be traced by use of a marker gene like β-galactosidase, and determine their histology as compared to tissues that develop normally and those that develop without the benefit of the developmental control of p53. Typical methods of monitoring include histologic analysis (microscopic, immunohistochemistry), protein analysis (Western blot, SDS-PAGE, 2D PAGE), TUNEL analysis. Assays for markers of terminal differentiation are also contemplated. These markers can be measured as expression of genes or proteins expressed in differentiated cells. Gene expression can be assayed using techniques well known to those of skill in the art, for example, by Northern Blotting, RNase protection assays, RT-PCR or a variety of other techniques. Proteins expressed can be assayed visually (e.g. the production of hemoglobin in differentiating ES cells) or by the other assays listed above.

2. Drosophila

Another system that may advantageously be employed in an in vivo context is *Drosophila melanogaster*. Drosophila genetics have been extensively studied and, thus, provide a fruitful starting point for analysis. One embodiment employs use of tissue specific promoters in Drosophila to drive the expression of a dominant negative p53 gene or a double minute-2 gene, thereby knocking out p53 functions in these cells. Because only certain tissues will be targeted, one can monitor the development, or lack thereof, of these tissues. Preferably, the tissues to be targeted are non-essential, i.e., the fly can develop and live, at least temporarily, without them. One example of such a promoter is the eyeless promoter. This regulatory element is specifically turned on in tissues destined for eye development. The activation of this promoter, when linked to a mutant p53 or double minute-2 gene, will result in the absence of eye tissue formation. This is a non-lethal defect that is easily observed. Other promoters that may prove useful include but are not limited to gal4 responsive promoter, heat shock promoter and hairy promoter.

As discussed above, the engineering of blastomeres primarily relies on transfer of gene (mutant p53, double minute-2) to cells, with or without marker genes. Once transformed in this manner, the developmental pattern of the cells will be disrupted by virtue of the developmentally regulated expression of the blocking gene. In the case of eyeless, the absence of eye development will indicate that the blocking gene is expressed and operating. Provision of a candidate inhibitor substance that is sufficient to override the block well permit eye development.

3. Mouse

Mice were the first transgenic mammals and this system remains one of the best tested systems for gene transfer into developing embryos. This system is more complex than the amphibian and insect systems described above, but the large amount of work that has been done provides a very high level of expertise in manipulating murine embryonic cells. Essentially, mouse embryo cells may be manipulated as described above.

Another option with this system in the generation of chimeric mice having both p53-blocked and unblocked cells. In some tissues the lack of p53 ultimately leads to death of the organism, but the present invention is useful in that chimeric mice may be generated that house lethally defective cells. Pluripotent stems cells can be removed from blastocysts and cultured in the presence of LIF to maintain totipotency. Once engineered to establish a p53 block (as discussed above), the cells can be introduced into a blastocoel. Implantation of the blastocyst into a foster mother, followed by gestation, results in a chimeric animal that has embryonic stem cells with both blocked an unblocked p53 differentiation patterns. Such animals may then provide in vivo models and be examined for abnormalities development arising from p53 abrogation.

Thus a transgenic mouse expressing mutant p53 can be generated and tested for its developmental abilities. Such an animal may be used to test the effectiveness of compounds isolated from other screens or for screening new compounds useful in blocking p53-related defects in cellular differentiation. The transgenic mouse can be generated by direct microinjection of DNA or mRNA encoding mutant p53, or by introducing ES cells expressing mutant p53 into embryos, then testing the compounds directly on these embryos following transplantation.

F. Candidate Substances

According to the present invention, one may screen any kind of candidate substance for activity in the assays described above. Although drug design principles may be employed, one of the advantages of the present invention is that large numbers of compounds may be screened i) Pharmaceuticals Any classic pharmaceutical may be tested according to the present invention. Useful compounds in this regard will include those compounds, and compounds related thereto, that are known to affect cellular development and tumorigenesis. Many classic pharmaceuticals are derived from naturally occurring compounds, and also may include fragments or parts of naturally-occurring compounds, or may be only found as active combinations of known compounds which are otherwise inactive.

Particularly fruitful sources for pharmaceuticals include bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

ii) Expression Libraries

Expression libraries, also known as cDNA libraries, comprises complementary DNA copies of mRNA's from a selected cell or tissue. These libraries represent the genetic information that is transcribed in the cells. The cDNA's are cloned into plasmids such that they are positioned under the control of regulatory signals that permit the transcription and translation of the mRNA produced therefrom.

In one embodiment, expression libraries may be used in a random fashion. These libraries are contacted with cells have a p53-related block in differentiation. After monitoring the effects that the library has on individual cells, cells which exhibit the desired characteristics can be isolated, and DNA therein analyzed. In this manner, the expression plasmid can be identified and the gene responsible for the desired characteristic sequenced.

In other embodiments, candidate members of an expression library may be utilized selectively, thereby obviating the need for later identification. This approach is more time consuming and permits only testing of selected clones. This generally requires that some additional criteria be used to narrow the candidate clones or genes.

iii) mRNA Pools

Messenger RNA's encode various proteins within a cell. It is possible to isolate mRNA's that are homogenous, or substantially homogeneous and use these molecules in "gene" transfer experiments, as discussed above. For example, it is possible to generate mRNA's in cell free systems using DNA's with the appropriate regulatory signals as the template. Large amounts of homogeneous RNA can be produced in this fashion.

Another approach to the production of mRNA's is to isolate whole cell or poly-A RNA's from tissues which have mRNA profiles that are predominated by a single species. This single species can be further purified in order to minimize the amount and number of contaminating minor species. Methods for isolating and handling mRNA's are well known to those of skill in the art.

iv) Small Molecule Libraries

Small molecule libraries include both peptides and organochemicals. These compounds generally are generated in an automated fashion. For example, peptides may be synthesized to substitute all possible variations at a single position. Series of peptides substituting for each residue in a peptide permit "scanning" of peptides for active sites. Similarly, organic molecules utilize substitution of various R-groups with structurally similar, but distinct, chemical units, such as alkyl, aryl, alkenyl, etc. Many such libraries are commercially available.

G. Mutagenesis

In a variation on the assays described above, another embodiment of the present invention involves the use of engineered embryonic cells to screen for molecules that are involved with p53 and its function as a regulator of differentiation. Basically, the initial steps are as described above—obtaining an undifferentiated embryonic cell and blocking the function of p53 therein. Rather than attempting to overcome the block by virtue of a drug, nucleic acid or protein, the engineered embryonic cell is mutagenized, for example, with radiation or a chemical DNA damaging agent. If the mutagenesis effects a change that results in the differentiation of the previously blocked cell, identification of the mutation should reveal a gene or regulatory sequence that interacts with p53 or plays a role in a p53-related process.

Identification of the mutagenized gene involves segregating the trait by means of breeding. Briefly, the mutagensis can be performed using chemical mutagens, irradiation and by P-element mediated mutagenesis to generate insertional mutants (Bingham et al., 1982, Cooley et al., 1988).

Once mutations, which can either enhance or suppress the developmental defect caused by expression of mutant p53, have been generated, they can be characterized using standard genetic methods. Firstly, the position of the mutation which genetically interacts with mutant p53 gene will be mapped by determining with which genetic markers it co-segregates. Meiotic recombination frequencies will then be used to map the genetic position of the mutation within the identified chromosome. Once the position of the mutation has been refined candidate genes will be identified, if possible, from the detailed genetic and DNA data bases available on Drosophila. If known genes or mutations map to the identified region, these will be obtained from the laboratories which identified them. If candidate genes or mutants can be obtained from other laboratories, these will be tested in genetic crosses to determine if they correspond to the identified mutation. If the mutations map in regions containing no previously identified genes or mutations the region will be cloned and analyzed in order to identify the responsible genes.

Cloning of the interacting mutants can be done in a number of ways. If the mutations have a phenotype in the absence of the mutant p53 P-element cloning can be achieved via a P-element mediated mutagenesis screen, whereby the transposition of endogenous P-elements is used to disrupt the genome via insertional mutagenesis (Cooley et al., 1988). If a P-element insertion in trans to the p53 interacting mutation generates the same phenotype as the interacting mutation in trans to itself, the insertion site is probably within the gene being sought. A genomic library can be made from these flies and the P-element DNA sequences used to isolated genomic fragments adjacent to the insertion site. If the mutations only generate a phenotype in the presence of the mutant p53 P-element the analysis will be more complex. In this instance fine genetic mapping followed by chromosome walking will be required to identify the responsible gene. Chromosome walking is achieved by making a stepwise progression through a genomic library using the extreme end of one clone to identify overlapping clones which correspond to sequences further along the chomosome. The extreme end of this new clone is then used to identify even more distant sequences, and so on.

Two classes of mutations can be identified in a screen such as the one described. Mutations which rescue (suppress) the block to differentiation imposed by mutant p53, and mutations which enhance the block to differentiation. Of course, mutations in the introduced P-element disrupting the introduced p53 gene will also be generated, but these will be detected and will be discarded from the screen. Mutations which enhance the mutant p53 mediated block to differentiation probably act with p53. during the normal differentiation process, and mutations inactivating such cofactors will contribute to the inhibition of differentiation. In this instance the mutations will be loss-of-function mutants, whereby the mutation has inactivated an interacting gene. Such loss-of-function muations may well have a developmental phenotype when in trans to themselves, even in the absence of the mutant p53 P-element, which will make their genetic and molecular characterization much more straightforward. Mutations which suppress the mutant p53 phenotype will probably be caused by gain-of-function (neomorphic) mutations. Such mutations either increase the level or activity of a gene or gene product in such a way as to over-ride the ability of mutant p53 to suppress this activity. Gain-of-function mutations also can impart novel activities upon a gene or gene product. Such mutants may or may not require the mutant p53 gene in order to cause a developmental defect.

Examples of genes which could be identified by such screening methods described above include mdm-2 null mice which die very early in development, and p53 null mice which survive. Mdm-2 null mice develop normally in a p53 null genetic background. In this example the p53 mutation suppresses, or negates, the requirement for mdm-2 activity. A mutagenesis study of mdm-2 null mice would have identified the p53 gene. In the examples proposed herein above the opposite approach is being taken: generate a p53 null phenotype, then screen for interacting genes.

H. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Mutant and wild-type p53 cDNAs, and Xdm-2 cDNA, were subcloned into the Xenopus expression vector pSP64TS which provides Xenopus globin 3' and 5' untranslated regions that significantly improve translation efficiency, with the exception of $p53^{His175}$, which was used in pBS-SK (Stratagene). Capped mRNA was transcribed in vitro (Krieg and Melton, 1984), and embryo handling, microinjections (2 to 5 nl) and β-galactosidase assays were performed as previously described (Vize et al., 1991). Embryos were staged according to P. Nieuwkoop and J. Faber (Nieuwkoop and Faber, 1994).

Embryos were fixed in MEMFA, stained for β-galactosidase activity (Vize et al., 1991) and processed in one of two ways. Some specimens were stained for antibodies 2G9 (neural), 12/101 (muscle), 3G8 (pronephros), or EPA (epidermis) using whole-mount immunocytochemistry, embedded in JB-4 (Polysciences), sectioned at 5μ, and counterstained with Sytox™ green (Molecular Probes) or hematoxylin and eosin (Sigma). Other specimens were embedded in Paraplast, sectioned at 10μ, and stained for antibodies 2G9, 12/101, or 3G8 using serial-section immunochemistry. This procedure yielded better penetration of the antibody into the specimens.

RT-PCR: Embryos were injected with 0.5 ng $p53\text{-}^{Thr280}$ into the marginal zone of all four cells at the four cell-stage; control embryos were uninjected. Total RNA was extracted from 5 embryo equivalents at stages 6, 10.5, and 13 and reverse transcribed. PCR was performed using one tenth of each reverse transcription reaction, Taq polymerase, 1 Ci of $^{32}$P-dATP, and primer sets listed below; cycle temperatures were 92° C., 55° C., and 72° C.; EF-1a for 16 cycles; goosecoid and brachyury for 19 cycles. Primer sets were as follows: EF-1α: CAGATTGGTGCTGGATATGC (SEQ ID NO:1) and ACTGCCTTGATGACTCCTAG (SEQ ID NO:2); goosecoid: ACAACTGGAAGCACTGGA (SEQ ID NO:3) and TCTTATTCCAGAGGAACC (SEQ ID NO:4); brachyury: GGATCGTTATCACCTCTG (SEQ ID NO:5) and GTGTAGTCTGTAGCAGCA (SEQ ID NO:6) One fifth of each PCR reaction was then electrophoresed on a 5% non-denaturing acrylamide gel and autoradiographed.

Example 2

Blocking Endogenous p53 Function in Xenopus Embryonic Cells

In order to inactivate the maternal stockpile of Xenopus p53, mRNA encoding a dominant-negative mutant form of p53 was introduced into developing embryos by microinjection. Synthetic mRNA encoding a dominant-negative form of human p53, $p53^{Thr280}$ (Sun et al., 1994), was microinjected into a single blastomere in the presumptive mesoderm of 32-cell stage embryos along with mRNA encoding nuclear β-galactosidase as a lineage tracer (Vize et al., 1991). These embryos were then raised to tadpole stages, fixed, and stained for β-galactosidase activity (FIG. 1). Injection of β-galactosidase mRNA alone had no effect on development (Table 2); and in such control experiments, β-galactosidase-positive cells were found evenly incorporated into axial. However, in embryos co-injected with $p53^{Thr280}$ mRNA, the β-galactosidase-positive cells derived from the injected blastomere were found to be clustered into large cell masses, with no organization into axial structures (FIG. 1; Table 2).

TABLE 2

Frequency of developmental tumor formation in response to ectopic expression of tumor-suppressors or proto-oncogenes.

| Injected mRNA | Tumor Frequency | N | # Expts. |
|---|---|---|---|
| 0.5 ng β-gal | 0% | 66 | 8 |
| 0.5 ng $p53^{Thr280}$ | 67% | 120 | 2 |
| 0.5 ng $p53^{Trp248}$ | 71% | 34 | 2 |

TABLE 2-continued

Frequency of developmental tumor formation in response to ectopic expression of tumor-suppressors or proto-oncogenes.

| Injected mRNA | Tumor Frequency | N | # Expts. |
|---|---|---|---|
| 0.5 ng Hp53 | 0% | 94 | 2 |
| 0.5 ng Xp53 | 0% | 38 | 1 |
| 1.0 ng xWT1 | 0% | 106 | 11 |
| 1.5 ng p53$^{His175}$ | 54% | 114 | 2 |
| 1.5 ng Xdm-2 | 30% | 249 | 4 |

Table 2. Wild-type tumor suppressors p53 (both human and Xenopus) and WT1 (Xenopus) do not induce tumor formation. Mutant p53 and wild-type Xdm-2 cause developmental tumors in a large percentage of injected embryos. The distribution of β-galactosidase-positive cells (see Table 3 and FIG. 2A) was used to score the frequency of tumor formation, and tumor phenotypes were confirmed by histology. p53$^{His175}$ was not cloned into the expression vector 64TS and mRNA was generated from pBS, such mRNA will have a significantly lower translation efficiency (Vize et al., 1991), which may explain the reduced frequency of tumor formation for this mutant. Abbreviations: β-gal, β-galactosidase; Xp53, Xenopus wild-type p53; Hp53, human wild-type p53; xWT1, Xenopus wild-type WT1 (Carroll and Vize, 1996).

TABLE 3

Wild-type p53 rescues the mutant p53 phenotype.

| Injected mRNA(s) | Tumor Freq. | N | # of Expts. |
|---|---|---|---|
| 125 pg p53$^{thr280}$ | 66% | 249 | 8 |
| 125 pg p53$^{thr280}$ + 500 pg Xenopus p53 | 30% | 113 | 5 |
| 125 pg p53$^{thr280}$ + 500 pg human p53 | 32% | 128 | 4 |

Figure 2A:
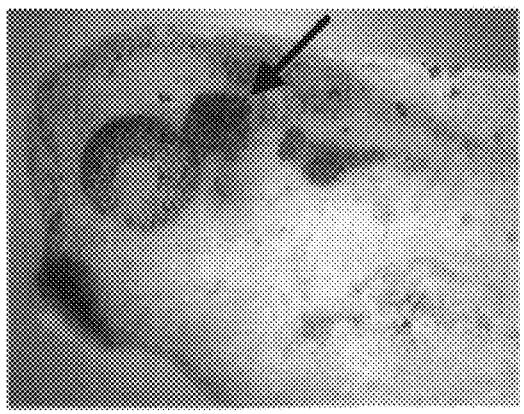
FIG. 2A and FIG. 2B. Wild-type p53 rescues the mutant p53 phenotype.
Figure 2B:
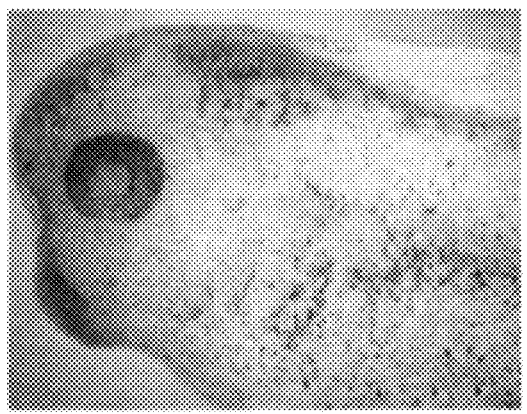
Figure 3A:
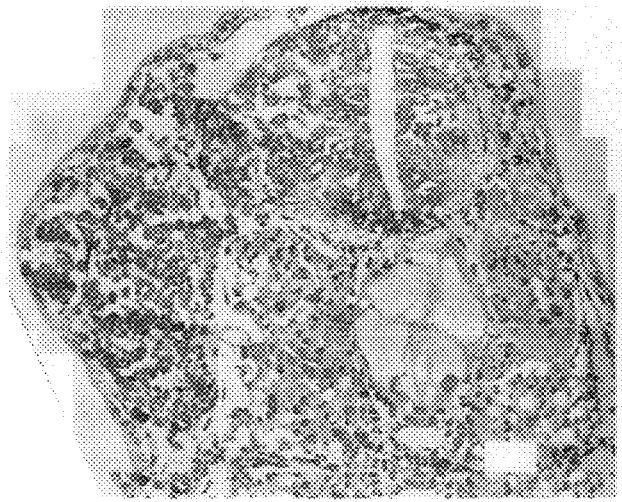
Figure 3B:
Figure 3C:
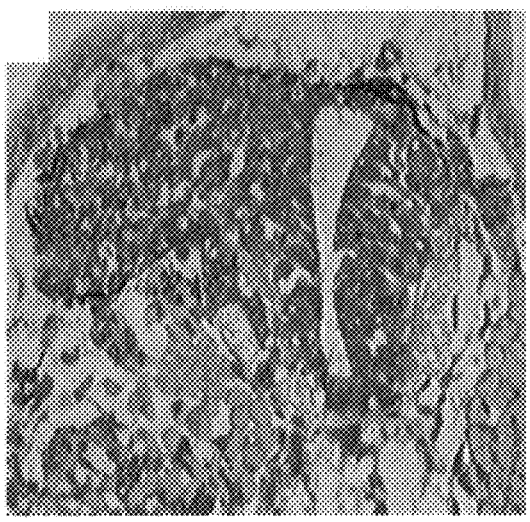
Figure 3D:
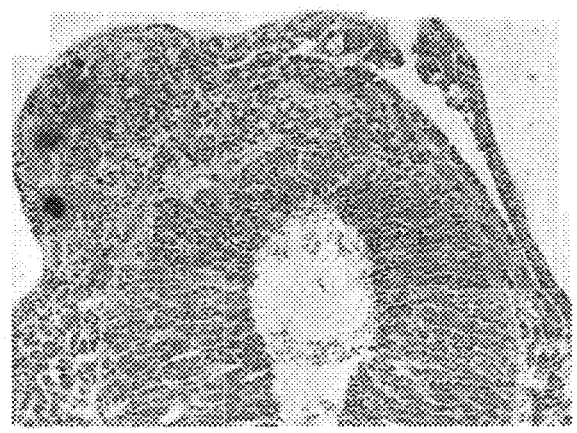

Table 3. The distribution of β-galactosidase-positive cells (as shown in FIG. 2A and FIG. 2B) was used to score the frequency of tumor formation in this assay, and tumor phenotypes were confirmed by histology. Four-fold overexpression of either Xenopus or human wild-type p53 reduced tumor frequency by more than half.

Histological analysis revealed that the cell masses formed by cells expressing p53$^{thr280}$ resembled tumors in a number of ways. The cell masses were nucleated and the cells within them were of approximately normal size and retained large numbers of yolk platelets, reminiscent of undifferentiated cells (FIG. 1). Furthermore, abnormal nuclear morphologies were observed (FIG. 1), and the undifferentiated cell masses were sometimes surrounded by an epithelial capsule and were often adjacent to large deposits of extracellular matrix. Immunohistochemistry with antibodies that detect neural- (FIG. 1), muscle-, epidermal- or pronephric-specific antigens failed to detect expression of any markers of terminal differentiation within p53$^{thr280}$-induced tumors. These cells remained undifferentiated through the latest stage examined (the feeding tadpole stage). As these tumors are derived from embryonic cells that have failed to differentiate, rather than from cells that have undergone dedifferentiation, they can be classified as blastomas, or undifferentiated embryonic-derived tumors.

Blocking p53 activity did not overtly interfere with or promote proliferation. As Xenopus early development proceeds without growth, cell division results in the formation of smaller and smaller cells with each cell cycle. When a single blastomere was injected with mutant p53, it gave rise to tumors containing hundreds of cells of approximately normal size, indicating that they have undergone a normal number of cell divisions. Although some tumor nuclei may be pycnotic, extensive apoptosis was not triggered by blocking p53 activity, as evidenced by the continued presence of β-galactosidase-positive tumor cells. These observations show that the formation of tumors is not the result of hyperproliferation, but rather is the result of the failure of cells to be incorporated into normal tissues and to undergo differentiation.

The phenotype elicited by mutant p53 was not due to non-specific effects caused by mRNA toxicity, as overexpression of wild-type human or Xenopus p53 did not induce tumor formation or inhibit normal differentiation (Table 2). While it has been previously reported that overexpression of wild-type Xenopus p53 results in cell cycle arrest (Hoever et al., 1994), the doses required to elicit such effects were extremely high, the lowest dose being more than double the highest dose injected here. In this study, injections of up to 1 ng of Xenopus or human wild-type p53 did not elicit cell cycle arrest or tumor formation. Likewise, injection of β-galactosidase mRNA alone, even at very high doses, had no effect on development (Table 2). Furthermore, no tumors have been reported in Xenopus embryos in previous studies where other gene products were ectopically expressed, including other tumor-suppressors such as APC (Vleminckx et al., 1997) and WT1 (Table 2), proto-oncogenes such as jun (Dong et al., 1996) and ras (Whitman and Melton, 1992), viral oncogenes such as polyoma middle T (Whitman and Melton, 1989) and v-ras (Whitman and Melton, 1992), or cyclins such as cyclin B2 (Hartley et al., 1996).

Example 3

Wild-type p53 Suppresses the Tumor-inducing Activity of Mutant p53

Although mutant human p53 was overexpressed in these experiments, Xenopus p53 is similar in structure and function to human p53 and can form functional heterotetramers with human p53 (Tchang et al., 1993; Wang et al., 1995). If the mutant p53 blocks differentiation by oligomerizing with and inhibiting the activity of the endogenous Xenopus p53 protein, the effect should be abrogated by coinjection with excess wild-type p53. Indeed, when an excess of either human or Xenopus wild-type p53 was coinjected with p53$^{thr280}$, the frequency of tumor formation was dramatically reduced (FIG. 2 and Table 3). Considering that p53 functions as a tetramer, most oligomers formed from a 4:1 mixture of wild-type to mutant p53 protein will contain at least one mutant subunit. This fact, in addition to the enhanced stability of mutant p53 proteins (Olson and Levine, 1994; Blagosklonny et al., 1995) may explain the inability of wild-type p53 to completely rescue the tumor phenotype.

Example 4

Different p53 Mutants Elicit a Similar Developmental Phenotype

It is possible that the tumor phenotype was the result of an activity unique to p53$^{thr280}$. Therefore, the activity of other p53 dominant-negative mutants was evaluated using identical protocols. The original mutant tested, p53$^{thr280}$, disrupts an essential base contact in the DNA-binding domain (Sun et al., 1994; Cho et al., 1994). Another mutant, p53$^{trp248}$, disrupts DNA binding by eliminating essential minor groove contacts (Cho et al., 1994). Expression of p53$^{Trp248}$ elicited a tumor phenotype identical to that of p53$^{Thr280}$ in terms of frequency (Table 2), size, gross morphology, and histology (FIG. 3). A third mutant, p53$^{His175}$ which disrupts protein folding in the DNA-binding domain (Cho et al., 1994), also elicited a similar tumor phenotype (FIG. 3, Table 2).

When embryos were injected into the presumptive somitic mesoderm, cells expressing a dominant-negative p53 were often displaced dorsally and lay adjacent to the neural tube just below the epidermis (FIG. 3). In many instances, such tumors were integrated into the differentiated cells of the adjacent epidermis or neural tube (FIG. 3). Many tumors had associated melanocytes, either superficial or integrated. The only other tissue in this region of the embryo with which melanocytes are commonly associated is the neural tube. In many cases where tumors were found lateral to the neural tube, the somite on the injected side of the embryo was restricted ventrally and greatly reduced in size (FIGS. 1 and 3). Although it is possible that this reduction of the somite may be a result of tissue distortion caused by the presence of the tumor, it is more likely due to the failure of $p53^{thr280}$-expressing cells to differentiate and consequent failure of these cells to contribute to the somitic tissue.

Figure 4A:
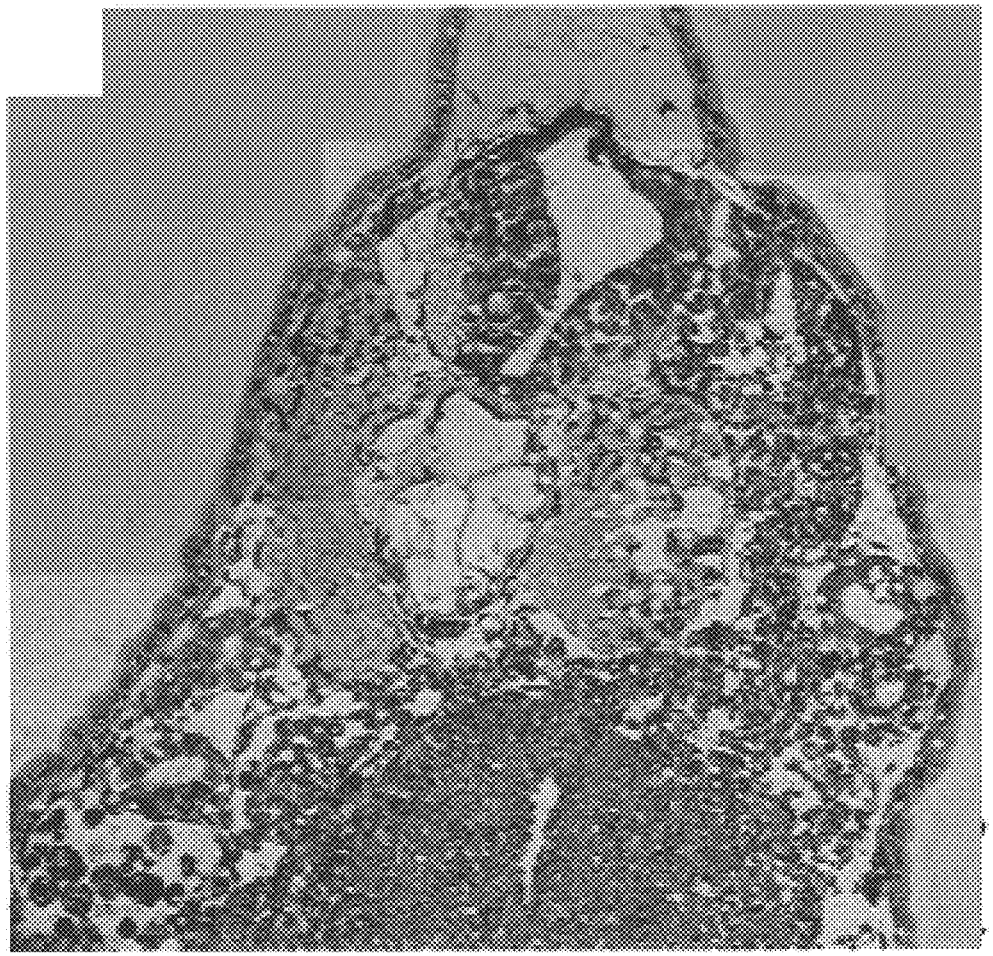
FIG. 4A and FIG. 4B. Developmental tumor associated with multiple tissues. Transverse section (FIG. 4A) and schematic diagram (FIG. 4B) illustrating a tumor (in this case $p53^{Trp248}$-induced) which is associated closely with the neural tube, extends under the notochord and is associated with the pronephros on the opposite side of the embryo. The right side was injected with mutant p53 mRNA. The presence of tumor cells on both sides of the midline is probably a consequence of the movement of loosely adherent cells driven by normal morphogenetic movements, rather than the undifferentiated cells possessing any invasive properties.
Figure 4B:
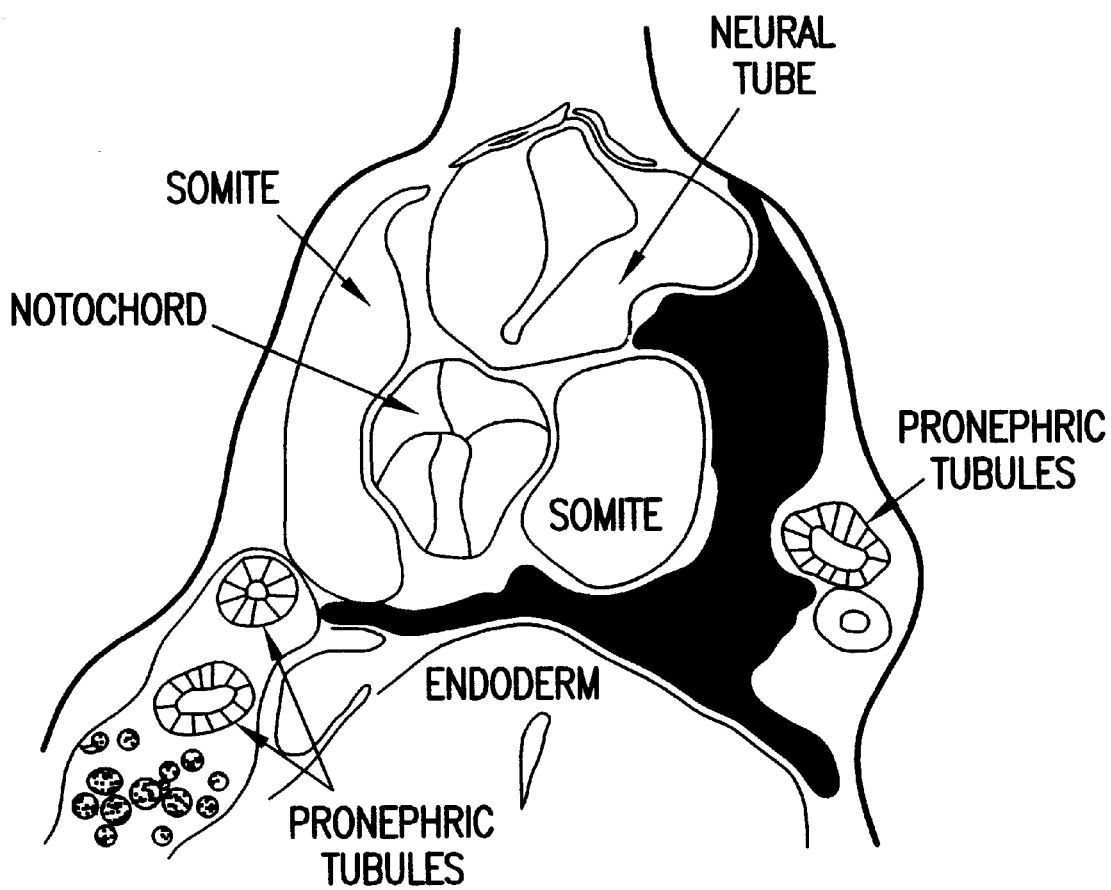

Tumors were also, though more rarely, found associated with mesodermal tissues such as somite and pronephros (FIG. 4). Because of the association of tumors with a number of different tissues, the ability of $p53^{thr280}$ expression to block differentiation was tested in several cell lineages. Expression of $p53^{thr280}$ inhibited differentiation and elicited tumor formation in presumptive somite, brain, spinal cord, pronephros, and epidermal lineages when assayed by histology and immunohistochemistry. Tumors derived from all cell types were similar to those described above for presumptive somite.

Example 5

Ectopic Xdm-2 Causes Tumor Formation

The observation that wild-type p53 can block the activity of a mutant protein and that three different p53 mutants induce similar tumors argues that the mutant human p53 proteins block differentiation by inhibiting the activity of endogenous Xenopus p53. However, it is possible that these different proteins possess a common gain-of-function (neomorphic) activity and act via other proteins not normally associated with wild-type p53. The inventors therefore sought to repress p53 activity without introducing mutant proteins.

The murine double minute-2 (mdm-2) gene encodes an oncoprotein which binds to and inhibits the activity of the p53 transcriptional activation domain (Kussie et al., 1996; Momand et al., 1992). In order to eliminate p53 activity, mRNA injection was used to overexpress the Xengpus ortholog of mdm-2, Xdm-2 (Kussie et al., 1996), in developing embryos. The expression of Xdm-2 during normal Xenopus development has not yet been described, however the developmental expression of this gene is not relevant to the experiments described here, as microinjected Xdm-2 was used only to interfere with the maternal stockpile of p53, not endogenous Xdm-2.

Overexpression of Xdm-2 mRNA elicited a tumor phenotype similar to that of mutant p53 (FIG. 3), although at a lower frequency (Table 2). These tumors were again identified initially by the failure of β-galactosidase-positive cells to incorporate normally into axial structures of the embryo. Tumors resulting from Xdm-2 overexpression were in general smaller than those elicited by mutant p53; however, histological analysis revealed that Xdm-2-induced tumors were similar in morphology to those resulting from mutant p53 expression (FIG. 3). Xdm-2-induced tumors tended to be located in aberrantly dorsal positions, contained yolk-filled, nucleated cells, and were sometimes integrated into the neural tube or epidermis (FIG. 3).

It is possible that Xdm-2 induces tumors at a lower frequency than mutant p53 because of differences in protein stability, stoichiometry of inhibitory mechanisms, or because Xdm-2 only possesses a subset of the activities of mutant p53. Xdm-2 may induce tumors by blocking endogenous p53 activity, while mutant p53 proteins may function both by blocking endogenous p53 and by gain-of-function activities (Dittmer et al., 1993). The early lethality observed in mdm-2 null mice can be rescued by generating such mice in a p53 null background, arguing that the only essential function of mdm-2 during normal development is the regulation of p53 activity (Montes de Oca Luna et al., 1995; Jones et al., 1995). Given this observation, it would seem that the Xdm-2 induced developmental tumors represent the minimal consequence of blocking p53 activity in Xenopus.

Example 6

Mutant p53 Does Not Interfere with the Mid-Blastula Transition

Figure 5:
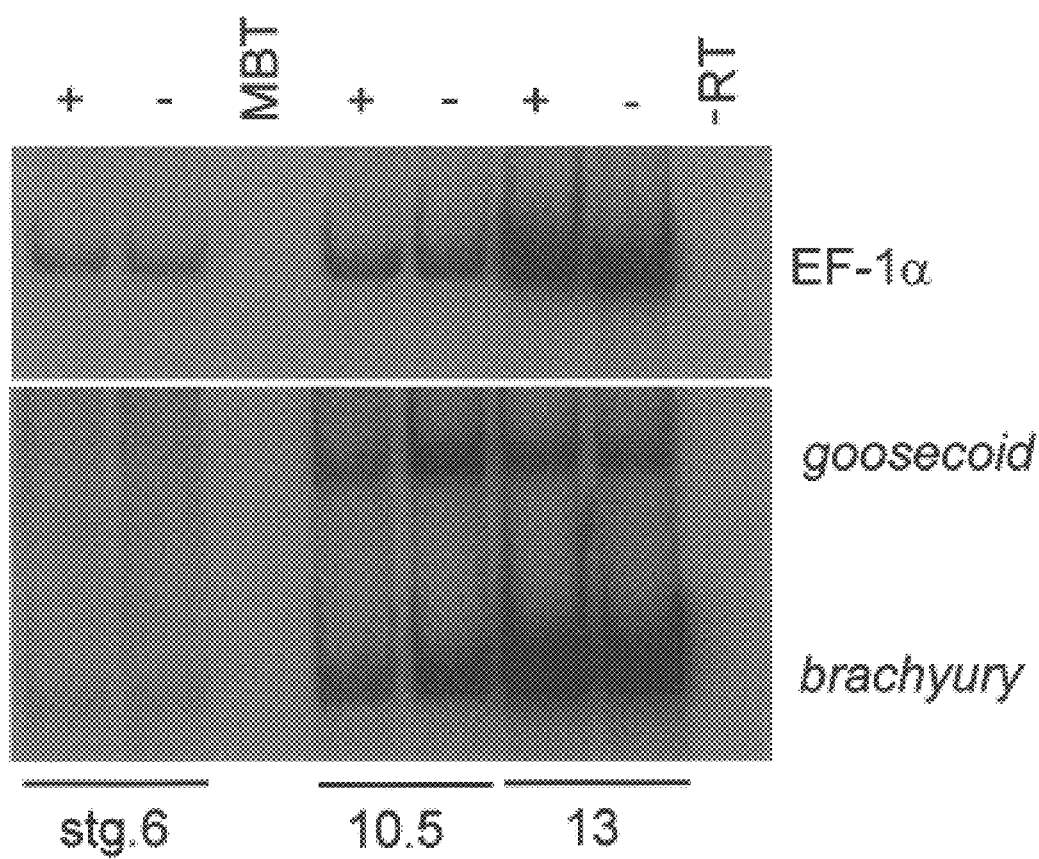
FIG. 5. Dominant-negative p53 does not inhibit the midblastula transition. 4-cell stage embryos were injected with $p53^{Thr280}$ mRNA into all four cells (+ samples), control embryos were uninjected (– samples). At stage 6 (lane 1-2), $p53^{Thr280}$ mRNA injected embryos (+) and uninjected embryos (–) both express low levels of EF-1a, but do not express goosecoid or brachyury. Following the MBT, at stage 10.5 (lane 4-5) and stage 13 (lane 6-7), EF-1a expression is upregulated and zygotic expression of goosecoid and brachyury commences equally in injected (+) and uninjected (–) embryos. -RT=no reverse transcriptase control.

In Xenopus embryos, the first 12 cell cycles do not contain G1 or G2 phases; the cell cycle acquires these phases only after the mid-blastula transition (MBT), concomitant with the onset of zygotic gene expression and the loss of cell cycle synchrony (Newport and Kirschner, 1982; Newport and Kirschner, 1982b). One possible role for p53 in early amphibian development could be to implement G1 and G2 cell cycle control at the MBT. In order to examine this possibility, the MBT was analyzed in embryos injected with $p53^{thr280}$ into all cells at the four-cell stage. Zygotic transcription was activated normally (FIG. 5) and the cell cycle became asynchronous at the MBT in embryos expressing $p53^{280}$ in all cells, indicating that the MBT occurred normally. Not only does general transcriptional activation commence normally, as indicated by the activation of a housekeeping gene, EF-1a (Krieg et al., 1989), but mesodermal gene expression also commences normally, as evidenced by the activation of Brachyury (Smith et al., 1991) and Goosecoid (Cho et al., 1991) expression. This indicates that the mutant p53 is not blocking mesoderm induction. Rather, mutant p53 seems to be acting by blocking cells' ability to act on these signals and differentiate into mesoderm.

Example 7

A Role for p53 in Development

Taken together, the results presented herein suggest a crucial role for p53 in early Xenopus development. Although dominant-negative p53 mutants may have gain-of-function activities, the Xdm-2. results argue that the mutant proteins are likely to be acting by interfering with endogenous p53. If a gain-of-function activity is responsible, this activity must be shared by three different mutants and a distinct tumor phenotype must be elicited by ectopic Xdm-2. Although this would be an extraordinary coincidence, the inventors aim to eliminate this possibility by interfering with p53 activity by other methods. The most likely explanation for the data presented here is that p53 activity is essential for normal development in Xenopus, and that interfering with p53 function results in blocking the ability of embryonic cells to differentiate.

How can p53 be essential to frog development but dispensable during murine development? One possibility is that p53 is required for a developmental process that is not utilized during murine development. The mostly likely candidate process was the mid-blastula transition, which is critical to frog development but has no true equivalent in mice. However, the data shown in FIG. 5 indicate that the MBT occurs normally and so cannot explain the incongruence between mouse and frog observations. The Xenopus embryonic cell cycle undergoes a second transition period a few cycles after the MBT. This second transition is known as the early gastrula transition (EGT) and is characterized by a significant lengthening of the gap phases of the cell cycle (Howe et al., 1995). This lengthening may reflect the acquisition of additional check points or other cell cycle properties, and it may be these additional properties which are essential for differentiation. The timing of the EGT is consistent with the defects observed in response to blocking p53 activity, as the first stage at which defects have been identified are early neurulae, shortly after the end of gastrulation.

Xenopus contain a large maternal stockpile of p53 mRNA and protein (Cox et al., 1994), while mammalian embryos express only low levels of p53 (Komarova et al., 1997) and maternal stocks of p53 have not yet been described. A maternal stockpile of p53 protein in p53 null mice cannot explain the lack of an early effect on mouse development as p53 null mice can be crossed and produce viable offspring (Armstrong et al., 1995). It is possible that the Xenopus stockpile is utilized for some as yet uncharacterized, but essential, developmental process.

Another possibility is that mice have genetic redundancies not present in frogs, making Xenopus more sensitive to p53 inhibition. For example, in mammals mutation of MyoD or Myf-5 does not disrupt myogenesis, but combination of the two mutants does (Rudnicki et al., 1993). The detailed analysis of MyoD alone would not have predicted a role for this important gene in muscle development in mice. Another useful example is the activins, which appear to be essential for mesoderm induction in Xenopus (Hemmatti-Brivanlou and Melton, 1992) but which are not required for mesoderm formation in mice (Matzuk et al., 1995a;. 1995b). Once again, excluding a role for this gene in development based solely upon the mouse mutant phenotype would have been premature. Lower vertebrates may have less complex redundancies protecting proliferation and differentiation, making them more dependent on p53 function. It is interesting to note that developmental defects in p53 null mice occur at different frequencies in different genetic backgrounds (Armstrong et al., 1995; Sah et al., 1995), implying that at least some such functional redundancies exist, and that without these redundancies p53 function is necessary for normal development.

High level expression of a potent dominant-negative p53 during early murine development may well have more penetrant effects than targeted p53 disruption, especially if mutant proteins possess a weak gain-of-function activity in addition to their dominant-negative activity. The commonly used p53$^{Val135}$ transgenic mice express a rather weak temperature sensitive mutant under the control of the p53 promoter (Harvey et al., 1995). As mutant proteins must be present in excess to interfere effectively with wild-type protein (Gottlieb and Oren, 1996), these mice may not really address this question. The inventors are presently examining the activity of p5 3$^{thr280}$ on very early murine development to explore this issue. If the existence of genetic redundancies is the reason for the lack of a penetrant phenotype in p53 null mice, the lack of such redundancies in Xenopus may provide a system in which the redundant genes can be identified. Microinjection of mutant p53 mRNA plus pools of mRNAs from mammalian cell lines and screening for the ability of such pools to suppress tumor formation may allow the identification of such genes. The identification of such genes, will be extremely relevant to the study of human tumorigenesis.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

Armnstrong, et al., "High-frequency developmental abnormalities in p53-deficient mice," *Curr. Biol.*, 5:931–936, 1995.

Baichwal and Sugden, "Vectors for gene transfer derived from animal DNA viruses:

Transient and stable expression of transferred genes" In: *Gene Transfer*, Kucherlapati R, ed., New York, Plenum Press, pp. 117–148, 1986.

Baker, et al., "Chromosome 17 deletions and p53 gene mutations in colorectal carcinomas," *Science*, 244: 217–221, 1989.

Benvenisty & Neshif, "Direction introduction of genes into rats and expression of the genes," *Proc. Nat. Acad Sci. USA*, 83:9551 –9555, 1986.

Bingham, et al., "The molecular basis of P-M hybrid dysgenesis: the role of the P element, a P-strain-specific transposon family", *Cell* 29(3):995–1004, 1982.

Blagosklonny, et al., "Geldapamycin selectively destabilizes and conformationally alters mutated p53," *Oncogene*, 11:933–939, 1995.

Carroll and Vize, "Wilms tumor suppressor gene is involved in the development of disparate kidney forms: evidence from expression in the Xenopus pronephros," *Dev. Dynamics*, 206:131–138, 1996.

Casey et al., "Growth suppressor of human breast cancer cells by the introduction of a wild-type p53 gene," *Oncogene*, 6:1791–1797, 1991.

Cech et al., "In vitro splicing of the ribosomal RNA precursor of Tetrahymena: involvement of a guanosine nucleotide in the excision of the intervening sequence." *Cell*, 27 (3 Pt 2) p487–96, 1981.

Chang et al., Foreign gene delivery and expression in hepatocytes using a hepatitis B virus vector. *Hepatology*, 14:124A, 1991.

Chen and Okayama, "High-efficiency transfection of mammalian cells by plasmid DNA," *Mol. Cell Biol.*, 7:2745–2752, 1987.

Cho, et al., "Crystal structure of a p53 tumor suppressor-DNA complex: understanding tumorigenic mutations," Science, 265:346–355, 1994.

Cho, et al., "Molecular nature of Spemann's organizer: the role of the Xenopus homeobox gene goosecoid," *Cell*, 67:1111–1120, 1991.

Coffin, "Retroviridae and their replication," In: Fields B N, Knipe D M, ed. Virology. New York: Raven Press, pp. 1437–1500, 1990.

Cooley, et al., "A. Insertional mutagenesis of the Drosophila genome with single P elements. Science. 239(4844) :1121–8, 1988.

Couch et al., "Immunization with types 4 and 7 adenovirus by selective infection of the intestinal tract," *Am. Rev. Resp. Dis.,* 88:394–403, 1963.

Coupar et al., "A general method for the construction of recombinant vaccinia virus expressing multiple foreign genes", *Gene,* 68:1–10, 1988.

Cox, et al., "Xenopus p53 is biochemically similar to the human tumour suppressor protein p53 and is induced upon DNA damage in somatic cells," *Oncogene,* 9:2951–2959, 1994.

d van der E b, "A new technique for the assay of infectivity of human adenovirus 5 DNA", *Virology,* 52:456–467, 1973.

Dittmer, et al., "Gain-of-function mutations in p53," *Nature Genetics,* 4:42–46, 1993.

Donehower and Bradley, "The tumor suppressor p53," *Biochim. Biophys. Acta,* 1155:181–205,.1993.

Donehower, et al., "Mice deficient for p53 are developmentally normal but susceptible to spontaneous tumours," *Nature,* 356:215–221, 1992.

Dong, et al., "AP-1/jun is required for early Xenopus development and mediates mesoderm induction by fibroblast growth factor but not by activin," *J. Biol. Chem.,* 271:9942–9946, 1996.

Dubensky et al., "Direct transfection of viral and plasmid DNA into the liver or spleen of mice," *Proc. Nat. Acad. Sci. USA,* 81:7529–7533, 1984.

Eliyahu, et al., "Overproduction of p53 antigen makes established cells highly tumorigenic," *Nature,* 316:158–60, 1985.

Fechheimer et al., "Transfection of mammalian cells with plasmid DNA by scrape loading and sonication loading," *Proc. Natl. Acad. Sci. USA,* 84:8463–8467, 1987.

Ferkol et al., "Regulation of the phosphoenolpyruvate carboxykinase/human factor IX gene introduced into the livers of adult rats by receptor-mediated gene transfer", *FASEB J.,* 7:1081–1091, 1993.

Finlay, et al., "The p53 proto-oncogene can act as a suppressor of transformation," *Cell,* 57:1083–1093, 1989.

Forster & Symons, "Self-cleavage of plus and minus RNAs of a virusoid and a structural model for the active sites," *Cell,* 49:211–220, 1987.

Fraley et al., "Entrapment of a bacterial plasmid in phospholipid vesicles: Potential for gene transfer," *Proc. Natl. Acad. Sci. USA,* 76:3348–3352, 1979.

Friedmann, "Progress towardihuman gene therapy," *Science,* 244:1275–1281, 1989.

Gerlach et al., "Construction of a plant disease resistance gene from the satellite RNA of tobacco rinspot virus," *Nature (London),* 328:802–805, 1987.

Ghosh and Bachhawat, "Targeting of liposomes to hepatocytes," In: Wu G, Wu C ed. Liver diseases, targeted diagnosis and therapy using specific receptors and ligands. New York: Marcel Dekker, pp. 87–104, 1991.

Ghosh-Choudhury et al., "Protein IX, a minor component of the human adenovirus capsid, is essential for the packaging of full-length genomes," *EMBO J.,* 6:1733–1739, 1987.

Gomez-Foix et al., "Adenovirus-mediated transfer of the muscle glycogen phosphorylase gene into hepatocytes confers altered regulation of glycogen," *J. Biol. Chem.,* 267:25129–25134, 1992.

Gopal, "Gene transfer method for transient gene expression, stable transfection, and cotransfection of suspension cell cultures," *Mol. Cell Biol.,* 5:1188–1190, 1985.

Gottlieb and Oren, "p53 in growth control and neoplasia," *Biochim. Biophys. Acta,* 1287:77–102, 1996.

Graeber, et al., "Hypoxia-mediated selection of cells with diminished apoptotic potential in solid tumours," *Nature,* 379:88–91, 1996.

Graham and Prevec, "Adenovirus-based expression vectors and recombinant vaccines," *Biotechnology,* 20:363–390, 1992.

Graham and Prevec, "Manipulation of adenovirus vector," In: E. J. Murray (ed.), Methods in Molecular Biology: Gene Transfer and Expression Protocol, Clifton, N J: Humana Press, 7:109–128, 1991.

Graham et al., "Translation of mammalian mRNA injected into Xenopus oocytes is specifically inhibited by antisense RNA," *J. Cell Biol.,* 101:1094–1099, 1985.

Graham et al., Characteristics of a human cell line transformed by DNA from human adenovirus type 5. *J. Gen. Virol.,* 36:59–72, 1977.

Grunhaus & Horwitz, "Adenovirus as cloning vector," *Seminar in Virology,* 3:237–252, 1992.

Haffner and Oren, "Biochemical properties and biological effects of p53," *Curr. Op. Genet. Dev.,* 1995, 5:84–90.

Hall and Lane, "Tumor suppressors: a developing role for p53?," *Curr. Biol.,* 7:R144–R147, 1997.

Hartley, et al., "In vivo regulation of the early embryonic cell cycle in Xenopus," *Dev. Biol.,* 173:408–419, 1996.

Harvey, et al., "A mutant p53 transgene accelerates tumour development in heterozygous but not nullizygous p53-deficient mice," *Nature Genetics,* 9:305–311, 1995.

Haupt, et al., "Mdm2 promotes the rapid degradation of p53. *Nature.* 387, 296–9. 1997

Hemmatti-Brivanlou and Melton, "A truncated activin receptor inhibits mesoderm induction and formation of axial structures in Xenopus embryos," *Nature,* 359:609–614, 1992.

Hermonat and Muzycska, "Use of adenoassociated virus as a mammalian DNA cloning vector: Transduction of neomycin resistance into mammalian tissue culture cells," *Proc. Nat. Acad Sci. USA,* 81:6466–6470, 1984.

Hersdorffer et al., "Efficient gene transfer in live mice using a unique retroviral packaging line," *DNA Cell Biol.,* 9:713–723, 1990.

Herz and Gerard, "Adenovirus-mediated transfer of low density lipoprotein receptor gene acutely accelerates cholesterol clearance in normal mice," *Proc. Natl. Acad. Sci. USA* 90:2812–2816, 1993.

Hoever, et al., "Overexpression of wild-type p53 interferes with normal development in *Xenopus laevis* embryos," *Oncogene,* 9:109–120, 1994.

Horwich et al., "Synthesis of hepadenovirus particles that contain replication-defective duck hepatitis B virus genomes in cultured HuH7 cells," *J. Virol.,* 64:642–650, 1990.

Howe, et al., "Identification of a novel developmental timer regulating the stability of embryonic cyclin a and a new somatic a-type cyclin at gastrulation," *Genes and Dev.,* 9:1164–1176, 1995.

Jenkins, et al., "Cellular immortalization by a cDNA clone encoding the transformation-associated phosphoprotein p53," *Nature,* 312:651–654, 1984.

Jones & Shenk, "Isolation of deletion and substitution mutanits of adenovirus type 5," *Cell,* 13:181–188, 1978.

Jones, et al., "Rescue of embryonic lethality in Mdm2-deficient mice by absence of p53," *Nature,* 378:206–208, 1995.

Joyce, "RNA evolution and the origins of life," *Nature,* 338:217–244, 1989.

Kaneda et al., "Increased expression of DNA cointroduced with nuclear protein in adult rat liver", *Science,* 243:375–378, 1989.

Karlsson et al., *EMBO J.,* 5:2377–2385, 1986.

Kato et al., "Expression of hepatitis β virus surface antigen in adult rat liver," *J. Biol. Chem.,* 266:3361–3364, 1991.

Kim and Cech "Three-dimensional model of the active site of the self-splicing rRNA precursor of Tetrahymena." *Proc Natl Acad Sci U S A,* 84 (24) p8788–92, 1987.

Klein et al., "High-velocity microprojectiles for delivering nucleic acids into living cells", *Nature,* 327:70–73, 1987.

Komarova, et al., "Transgenic mice with p53-responsive lacZ: p53 activity varies dramatically during normal development and determines readiation and drug sensitivty in vivo," *EMBO J.,* 16:1391–1400, 1997.

Krieg and Melton, "Functional messenger RNAs are produced by SP6 in vitro transcription of cloned cDNAs, *Nucleic Acids Res.,* 12:7057–7070, 1984.

Krieg, et al., "The mRNA encoding elongation factor alpha (EF1-alpha) is a major transcript at the mid-blastula transition in Xenopus," *Dev. Biol.,* 133:93–100, 1989.

Kubbutat, et al., "Regulation of p53 stability by Mdm2", *Nature* 387, 299–303, 1997 Kussie, et al., "Structure of the MDM2 oncoprotein bound to the p53 tumor suppressor transactivation domain," *Science,* 274:948–953, 1996.

Le Gal La Salle et al., "An adenovirus vector for gene transfer into neurons and glia in the brain," *Science,* 259:988–990, 1993.

Levine, et al., "Selective disruption of E-cadherin function in early Xenopus embryos by a dominant negative mutant," *Development,* 120:901–909, 1994.

Levrero et al., *Gene,* 101: 195–202, 1991.

Macejak and Sarnow, *Nature,* 353:90–94, 1991.

Mann et al., "Construction of a retrovirus packaging mutant and its use to produce helper-free defective retrovirus", *Cell,* 33:153–159, 1983.

Markowitz et al., "A safe packaging line for gene transfer: Separating viral genes on two different plasmids," *J. Virol.,* 62:1120–1124, 1988.

Matzuk, et al., "Different phenotypes for mice deficient in either activins or activin recptor type II," *Nature,* 374:356–360, 1995b.

Matzuk, et al., "Functional analysis of activins during mammalian development," *Nature,* 374:354–356, 1995a.

Mercer et al., "Negative growth regulation in a glioblastoma tumor cell line that conditionally expresses human wild-type p53," *Proc. Natl. Acad Sci. USA,* 87:6166–6170, 1990.

Michel & Westhof, "Modeling of the three-dimensional architecture of group I catalytic introns based on comparative sequence analysis," *J. Mol. Biol.,* 216:585–610, 1990.

Molenaar, et al., "XTcf-3 transcription factor mediates beta-catenin-induced axis formation in Xenopus embryos," *Cell,* 86:391–399, 1996.

Momand, et al., "The mdm-2 oncogene product forms a complex with the p53 protein and inhibits p53-mediated transactivation," *Cell,* 69:1237–1245, 1992.

Montenarh "Biochemical properties of the growth suppressor/oncoprotein p53." *Oncogene* 7 (9) p1673–80, 1992.

Montes de Oca Luna, et al., "Rescue of early embryonic lethality in mdm2-deficient mice by deletion of p53," *Nature,* 378:203–206, 1995.

Mulligan, "The basic science of gene therapy," *Science,* 260:926–932, 1993.

Myers, EP 0273085

Newport and Kirschner, "A major developmental transition in early Xenopus embryos: I. characterization and timing of cellular changes at the midblastula stage," *Cell,* 30:675–686, 1982a.

Newport and Kirschner, "A major developmental transition in early Xenopus embryos: II. Control of the onset of transcription," *Cell,* 30:687–96, 1982b.

Nicolas & Rubenstein, "Retroviral vectors," In: Vectors: *A survey of molecular cloning vectors and their uses,* Rodriguez & Denhardt (eds.), Stoneham: Butterworth, pp. 493–513, 1988.

Nicolau et al., "Liposomes as carriers for in vivo gene transfer and expression," *Methods Enzymol.,* 149:157–176, 1987.

Nieuwkoop and Faber, "Normal Table of *Xenopus laevis* (Daudin)," New York, Garland, 1994.

Nigro, et al., "Mutations in the p53 gene occur in diverse human tumor types," *Nature,* 342:705–708, 1989.

O'Reilly, et al., "Patterning of the mesoderm in Xenopus: dose-dependent and synergistic effects of Brachyury and Pintallavis. Development. 121(5):1351–9, 1995 May.

Oliner et al. Nature 358: 80–83, 1992.

Olson and Levine, "The properties of p53 proteins selected for the loss of suppression of transformation," *Cell Growth and Diff,* 5:61–71, 1994.

Parada, et al., "Cooperation between gene encoding p53 tumour antigen and ras in cellular transformation," *Nature,* 312:649–651, 1984.

Paskind et al., "Dependence of moloney murine leukemia virus production on cell growth" *Virology,* 67:242–248, 1975.

Pelletier and Sonenberg, *Nature,* 334:320–325, 1988.

Perales et al., "Gene transfer in vivo: Sustained expression and regulation of genes introduced into the liver by receptor-targeted uptake", *Proc. Natl. Acad Sci.* 91:4086–4090, 1994.

Potter et al., "Enhancer-dependent expression of human k immunoglobulin genes introduced into mouse pre-B lymphocytes by electroporation," *Proc. Nat. Acad. Sci. USA,* 81:7161–7165, 1984.

Racher et al., *Biotechnology Techniques,* 9:169–174, 1995.

Ragot et al., "Efficient adenovirus-mediated transfer of a human minidystrophin gene to skeletal muscle of mdx mice," *Nature,* 361:647–650, 1993.

Reinhold-Hurek & Shub, "Self-splicing introns in tRNA genes of widely divergent bacteria," *Nature,* 357:173–176, 1992.

Renan, "Cancer genes: Current status, future prospects and applications in radiotherapy/oncology," *Radiother. Oncol.,* 19:197–218, 1990.

Rich et al., "Development and analysis of recombinant adenoviruses for gene therapy of cystic fibrosis," *Hum. Gene Ther.,* 4:461–476, 1993.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell BioL,* 10:689–695, 1990.

Rosenfeld et al., "Adenovirus-mediated transfer of a recombinant α1-antitrypsin gene to the lung epithelium in vivo," *Science,* 252:431–434, 1991.

Rosenfeld et al., "In vivo. transfer of the human cystic fibrosis transmembrane conductance regulator gene to the airway epithelium," *Cell,* 68:143–155, 1992.

Roth et al., "Retrovirus mediated wild-type p53 gene transfer to tumors of patients with lung cancer" *Nature Med.* 2(9):985–991, 1996.

Rotter, et al., "Does wild-type p53 play a role in normal cell differentiation?," *Sem. Cancer Biol.,* 5:229–236, 1994.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses", *Proc. Nat'l Acad. Sci. USA,* 86:9079–9083, 1989.

Rudnicki, et al., "MyoD or Myf-5 is required for the formation of skeletal muscle," *Cell,* 75:1351–1359, 1993.

Sah, et al., "A subset of p53 deficient mice exhibit exencephally," *Nature Genetics,* 10:175–180, 1995.

Sarnow, et al., "Adenovirus E1b-58kd tumor antigen and SV40 large tumor antigen are physically associated with the same 54 kd cellular protein in transformed cells. *Cell* 28: 387–394, 1982;

Sarver et al., "Ribozymes as potential anti-HIV-1 therapeutic agents," *Science,* 247:1222–1225, 1990.

Scanlon et al., "Ribozyme-mediated cleavages of c-fos mRNA reduce gene expression of DNA synthesis enzymes and metallothionein," *Proc Natl Acad Sci USA,* 88:10591–10595, 1991.

Scheffner, et al., "The E6 oncoprotein encoded by human papillomavirus types 16 and 18 promotes the degradation of p53", *Cell* 63: 1129–1136, 1990.

Scheffner, et al., "the HPV-16 E6 and E6-AP complex functions as a ubiquitin-protein ligase in the ubiquitination of p53", *Cell* 75: 495–505, 1993.

Schmid, et al., "Expression of p53 during mouse embryogenesis," *Development,* 113:857–65, 1991.

Smith, et al., "Expression of a Xenopus homolog of Brachyury (T) is an immediate-early response to mesoderm induction," *Cell,* 67:79–87, 1991.

Smith, et al., "Expression cloning of noggin, a new dorsalizing factor localized to the Spemann organizer in Xenopus embryos", *Cell:*70(5):829–40, 1992

Smith, et al., "Injected Xwnt-8 RNA acts early in Xenopus embryos to promote formation of a vegetal dorsalizing center", *Cell.* 67(4):753–65, 1991

Sokol, et al., "Injected Wnt RNA induces a complete body axis in Xenopus embryos", *Cell.* 67(4):741–52, 1991.

Stratford-Perricaudet & Perricaudet," Gene transfer into animals: the promise of adenovirus," p. 51–61, In: Human Gene Transfer, Cohen-Haguenauer & Boiron (eds.), Editions John Libbey Eurotext, France, 1991.

Stratford-Perricaudet et al., "Evaluation of the transfer and expression in mice of an enzyme-encoding gene using a human adenovirus vector", *Hum. Gene. Ther.,* 1:241–256, 1990.

Sun, et al., "Dosage dependent dominance over wild-type p53 of a mutant p53 isolated from nasopharyngeal carcinoma," *FASEB J.,* 7:944–950, 1994.

Takahashi et al., "The p53 gene is very frequently mutated in small-cell lung cancer with a distinct nucleotide substitution pattern," *Cancer Res.,* 52:734–736, 1992.

Tchang, et al., "Stabilization and expression of high levels of p53 during early development in *Xenopus laevis,"* *Dev. Biol.,* 159:163–172, 1993.

Temin, "Retrovirus vectors for gene transfer: Efficient integration into and expression of exogenous DNA in vertebrate cell genome," In: *Gene Transfer,* Kucherlapati (ed.), New York: Plenum Press, pp. 149–188, 1986.

Top et al., "Immunization :with live types 7 and 4 adenovirus vaccines. II. Antibody response and protective effect against acute respiratory disease due to adenovirus type 7," *J. Infect. Dis.,* 124:155–160, 1971.

Tur-Kaspa et al., "Use of electroporation to introduce biologically active foreign genes into primary rat hepatocytes", *Mol. Cell Biol,* 6:716–718, 1986.

Varmus et al., "Retroviruses as mutagens: Insertion and excision of a nontransforming provirus alter the expression of a resident transformning provirus," *Cell,* 25:23–36, 1981.

Vize, et al., "Assays for gene function in developing Xenopus embryos," *Meth. Cell Biol.,* 36:367–387, 1991.

Vleminckx, et al., "Adenomatous polyposis coli tumor suppressor protein has signalling activity in *Xenopus laevis* embryos resulting in the induction of an ectopic dorsoanterior axis," *J. Cell Biol.,* 136:411–420, 1997.

Wagner et al., *Proc. Natl. Acad Sci.* 87(9):3410–3414, 1990.

Wang, et al., *"Xenopus laevis* p53 protein: sequence-specific DNA binding, transcriptional egulation and oligomerization are evolutionarily conserved," *Oncogene,* 19:779–784, 1995.

Weinberg, "Tumor suppressor gene," *Science,* 254:1138–1145, 1991.

Whitman and Melton, "Induction of mesoderm by a viral oncogene in early Xenopus embryos," *Science,* 244:803–806, 1989.

Whitman and Melton, "Involvement of p21ras in Xenopus mesoderm induction," *Nature,* 357:252–254, 1992.

Wong et al., "Appearance of β-lactamase activity in animal cells upon liposome mediated gene transfer," *Gene,* 10:87–94, 1980.

Woodland, et al., "The development of an assay to detect mRNAs that affect early development", *Development.* 101(4):925–30, 1987.

Wu and Wu, "Evidence for targeted gene delivery to HepG2 hepatoma cells in vitro," *Biochemistry,* 27:887–892, 1988.

Wu and Wu, "Receptor-mediated in vitro gene transfections by a soluble DNA carrier system," *J. Biol. Chem.,* 262:4429–4432, 1987.

Wu and Wu, *Adv. Drug Delivery Rev.,* 12:159–167, 1993.

Yang et al., "In vivo and in vitro gene transfer to mammalian somatic cells by particle bombardment," *Proc. Natl. Acad Sci USA,* 87:9568–9572, 1990.

Yew and Berk, "Inhibition of p53 transactivation required for transformation by adenovirus early 1B protein", *Nature* 357, 82–85, 1992.

Zelenin et al., "High-velocity mechanical DNA transfer of the chloramphenicol acetyltransferase gene into rodent liver, kidney and manmmary gland cells in organ explants and in vivo", *FEBS Lett.,* 280:94–96, 1991.

What is claimed is:

1. A method of screening for agents that inhibit a block of p53-related embryonic cell differentiation comprising the steps of:

(i) providing an isolated, undifferentiated embryonic cell;
   (ii) blocking the function of p53 in said cell such that said cell fails to differentiate;
   (iii) contacting said cell with a candidate agent; and
   (iv) comparing the differentiation of said contacted cell after said contacting with the differentiation of said cell in the absence of said candidate agent;

whereby an increase in differentiation indicates that said candidate agent is an inhibitor of the block of p53-related differentiation.

2. The method of claim 1, further comprising the step of comparing the differentiation of said cell after said contacting with the differentiation of said undifferentiated embryonic cell.

3. The method of claim 1, wherein said cell is a mammalian cell.

4. The method of claim 3, wherein said cell is a mouse cell.

5. The method of claim 3, wherein said cell is a human cell.

6. The method of claim 1, wherein said blocking is achieved by introducing into said cell a nucleic acid encoding a dominant negative mutant of p53.

7. The method of claim 6, wherein said introducing is achieved via electroporation, microinjection, particle bombardment, liposome transfer or viral infection.

8. The method of claim 6, wherein said nucleic acid is a DNA.

9. The method of claim 6, wherein said nucleic acid is an RNA.

10. The method of claim 1, wherein said candidate agent is polypeptide.

11. The method of claim 1, wherein said candidate agent is produced by a neighboring cell.

12. The method of claim 11, wherein said neighboring cell is a second undifferentiated embryonic cell into which said candidate.agent has been introduced.

13. The method of claim 1, wherein differentiation is determined by culture of said undifferentiated embryonic cell in vitro under conditions where said cell differentiates.

* * * * *

UNITED STATES PATENT AND TRADEMARK OFFICE
CERTIFICATE OF CORRECTION

PATENT NO.      : 6,479,285 B1
DATED           : November 12, 2002
INVENTOR(S)     : Peter D. Vize and John B. Wallingford It is certified that error appears in the above-identified patent and that said Letters Patent is hereby corrected as shown below:

<u>Title page,</u>
Item [54], please delete "P53" and insert -- p53 -- therefor.

<u>Column 42,</u>
Line 3, please delete "." after "candidate."

<u>Column 7,</u>
Line 23, please delete "InhibitingpS3" and insert -- Inhibiting p53 -- therefor.

<u>Column 17,</u>
Line 5, please delete "embrydos" and insert -- embryos -- therefor.

Signed and Sealed this

Twenty-fifth Day of February, 2003

JAMES E. ROGAN
*Director of the United States Patent and Trademark Office*